US007807379B2

(12) United States Patent
Holten-Andersen et al.

(10) Patent No.: US 7,807,379 B2
(45) Date of Patent: Oct. 5, 2010

(54) TISSUE INHIBITOR OF MATRIX METALLOPROTEINASES TYPE-1 (TIMP-1) AS A CANCER MARKER

(75) Inventors: Mads Holten-Andersen, Copenhagen Ø (DK); Ross Stephens, Braddon (AU); Hans Jørgen Nielsen, Lyngby (DK); Ib Jarle Christensen, Hillerød (DK); Nils Brünner, Hellerup (DK)

(73) Assignee: Rigshospitalet, Copenhagen (DK)

( * ) Notice: Subject to any disclaimer, the term of this patent is extended or adjusted under 35 U.S.C. 154(b) by 0 days.

(21) Appl. No.: 11/449,869

(22) Filed: Jun. 9, 2006

(65) Prior Publication Data

US 2007/0020707 A1 Jan. 25, 2007

Related U.S. Application Data

(62) Division of application No. 09/546,573, filed on Apr. 10, 2000, now Pat. No. 7,108,983.

(30) Foreign Application Priority Data

Apr. 9, 1999 (DK) ................................ 1999 00476

(51) Int. Cl.
*G01N 33/53* (2006.01)
(52) U.S. Cl. ..................................... 435/7.1; 424/130.1
(58) Field of Classification Search ........................ None
See application file for complete search history.

(56) References Cited

U.S. PATENT DOCUMENTS

| 5,324,634 | A | 6/1994 | Zucker |
| 5,356,817 | A | 10/1994 | Cole |
| 5,643,752 | A | 7/1997 | Hawkins et al. |
| 7,108,983 | B1 | 9/2006 | Holten-Andersen et al. |
| 2002/0012950 | A1 | 1/2002 | Nielsen et al. |
| 2003/0082652 | A1 | 5/2003 | Holten-Andersen et al. |
| 2004/0014190 | A1 | 1/2004 | Lawrence et al. |
| 2004/0105862 | A1 | 6/2004 | Pan et al. |
| 2004/0157278 | A1 | 8/2004 | Astle et al. |
| 2006/0014224 | A1 | 1/2006 | Brunner et al. |
| 2006/0154245 | A1 | 7/2006 | Hessel et al. |
| 2008/0261246 | A1 | 10/2008 | Holten Andersen |
| 2009/0035794 | A1 | 2/2009 | Hessel |

FOREIGN PATENT DOCUMENTS

| CN | 1236102 A | 11/1999 |
| DK | PA1999 00476 | 4/1999 |
| EP | 1171771 | 10/2000 |
| EP | 1381631 | 10/2002 |
| EP | 1382969 | 1/2004 |
| EP | 1 439 393 | 7/2004 |
| JP | 0813654 A | 5/1996 |
| JP | 08136548 A2 | 5/1996 |
| JP | 8226918 A | 9/1996 |
| WO | WO 93/20447 | 10/1993 |
| WO | WO 97/38314 | 10/1997 |
| WO | WO 00/20860 A | 4/2000 |
| WO | 00/62070 | 10/2000 |
| WO | 01/11359 A2 | 1/2001 |
| WO | 02/34776 | 10/2001 |
| WO | 0231507 A2 | 4/2002 |
| WO | WO 02/44736 | 6/2002 |
| WO | 02/086085 A | 10/2002 |
| WO | 03/006671 A | 1/2003 |
| WO | WO 03/060522 | 2/2003 |
| WO | 03/087830 | 10/2003 |
| WO | WO 2004/029627 | 4/2004 |
| WO | WO 2005/010213 | 2/2005 |

OTHER PUBLICATIONS

Agresti, Alan. 1996. An Introduction to Categorical Data Analysis. John Wiley and Sons, Inc. 1996.*
"Concentrations of TIMP-1 mRNA Splice Variants and TIMP-1 Protein are Differentially Associated with Prognosis in Primary Breast Cancer" Anieta M. Sieuwerts et al., Clinical Chemistry 53:7, 1280-1288 (2007).
Wu Thomas D. "Analysing gene expression data from DNA microarrays to identify candidate genes" Journal of Pathology, J Pathol 2001, 195:53-65.
Lucentini Jack "Gene Association Studies Typically Wrong" The Scientist Dec. 20, 2004.
Keyszer G, Lambiri I, Nagel R, Keysser C, Keysser M, Gromnica-Ihle E, Franz J, Burmester GR, Jung K (1999) Circulating levels of matrix metalloproteinases MMP-3 and MMP-1, tissue inhibitor of metalloproteinases (TIMP-1), and MMP-1/TIMP-1 complex in rheumatic disease. Correlation with clinical activity of rheumatoid arthritis versus other surrogate markers. *J. Rheum.* 26:2, 251-258.
Khokha R & Waterhouse P (1994) The role of tissue inhibitor of metalloproteinase-1 in specific aspects of cancer progression and reproduction. *J.Neurooncol.* 18, 123-127.
Khokha R, Zimmer MJ, Wilson SM & Chambers AF (1992b) Upregulation of TIMP-1 expression in B16-F10 melanoma cells suppresses their metastatic ability in chick embryo. *Clin.Exp.Metastasis* 10, 365-370.
Kodama S, Yamashita K, Kishi J, Iwata K & Hayakawa T (1989) A sandwich enzyme immunoassay for collagenase inhibitor using monoclonal antibodies. *Matrix* 9, 1-6.
McDougall JR & Matrisian LM (1995) Contributions of tumor and stromal matrix metalloproteinases to tumor progression, invasion and metastasis. Cancer Metastasis Rev. 14, 351-362.
Matrisian LM (1992) The matrix-degrading metalloproteinases. Bioessays 14, 455-463.

(Continued)

*Primary Examiner*—Larry R. Helms
*Assistant Examiner*—Meera Natarajan
(74) *Attorney, Agent, or Firm*—Stanislaus Aksman; Roberts Mlotkowski Safran & Cole, P.C.

(57) ABSTRACT

The present invention describes a method for determining whether an individual is likely to suffer from cancer by determining a parameter representing the TIMP-1 concentration in body fluid samples from the individual.

29 Claims, 20 Drawing Sheets

OTHER PUBLICATIONS

Figure 1:
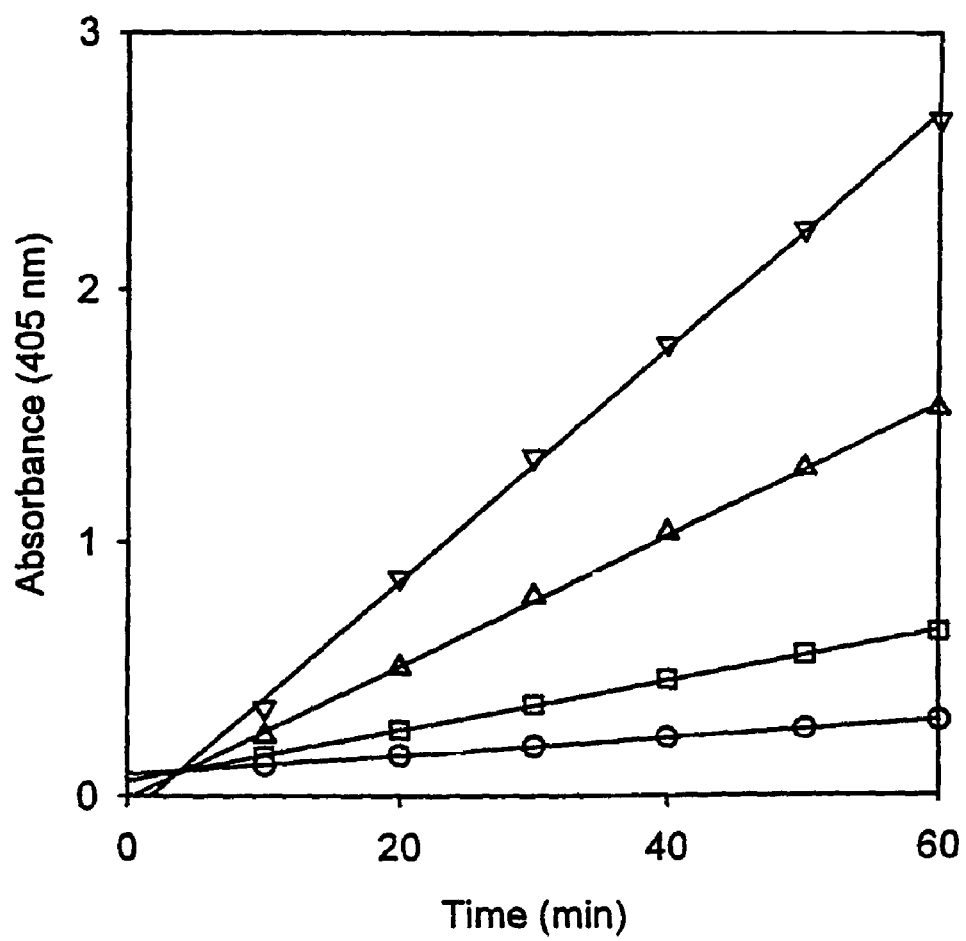

Mimori K, Mori M, Shiraishi T, Fujie T, Baba K, Haraguchi M, Abe R, Ueo H & Akiyoshi T (1997) Clinical significance of tissue inhibitor of metalloproteinase expression in gastric carcinoma. *Br.J.Cancer* 76, 531-536.

Moutsiakis D, Mancuso P, Krutzsch H, Stetler-Stevenson WG & Zucker S (1992) Characterization of metalloproteinases and tissue inhibitors of metalloproteinase's in human plasma. *Connect. Tissue Res.* 28, 213-230.

Kuska, J. Natl. Cancer Int, 90:564-565, 1998.

Jarzarb et al., Cancer Res., 65: (4) 1587-1597, 2005.

Zweig et al. "Receiver Operating Characteristic (ROC) Plots: A Fundamental Evaluation Tool in Clinical Medicine" Clinical Chem. 39/4, pp. 561-577 (1993).

Vincent Leroy et al., "Circulating Matrix Metalloproteinases 1, 2, 9 and Their Inhibitors TIMP-1 and TIMP-2 as Serum Markers of Liver Fibrosis With Chronic Hepatitis C: Comparison with PIIINP and Hyaluronic Acid" American Journal of Gastroenterology, 2004 (pp. 271-279).

Jung K, Nowak L, Lein M, Priem F, Schnorr D, Loening SA (1997) Matrix metalloproteinases 1 and 3, tissue inhibitor of metalloproteinase-1 and the complex of metalloproteinase-1/tissue inhibitor in plasma of patients with prostate cancer. *Int. J. Cancer* 74, 220-223.

Timo Sorsa et al. "Scientific Basis of a Matrix Metalloproteinase-8 Specific Chair-side Test for Monitoring Periodontal and Peri-implant Health and Disease" Annals of New York Academy of Sciences, vol. 878, 1999 pp. 130-140.

Cell and Tumor Biology 14: Protease Inhibitors in Invasion and Metastasis, "Proceedings of the American Association for Cancer Research", Mar. 1998, pp. 298-299, vol. 39.

Japanese Office Action for Japanese Application No. 2000-611082 dated Jan. 6, 2010 from JPO and English Translation.

U.S. Appl. No. 10/594,999, filed Sep. 29, 2006, Maria Unni Romer et al.

Schrohl Anne-Sofie et al: Tumor tissue concentrations of the proteinase inhibitors Tissue Inhibitor of metalloproteinases-1 (TIMP-1) and Plasminogen Activator Inhibitor type 1 are complimentary in determining prognosis in primary breast cancer Mollecullar and Cellular Proteomics vol. 2, No. 3, pp. 164-172 2003 by the American Society of Biochemistry and Molecular Biology, Inc.

Kwaan H C et al: "Plasminogen activator inhibitor 1 may promote tumour growth through inhibition of apoptosis" British Journal of Cancer (2000) 82(10), pp. 1702-1708.

Simpson Ram et al. Colorectal Dis. 2000; 2:100-5.

Pellegrini P. et al Cancer Immunol Immuunother Sep. 2000; 49 (7) 388:94.

Matsuura E. et al J. Neurol Sci. 2000; 173:45-52.

Jinnin M et al Clin Exp Rheumatol Jul.-Aug. 2002; 20 (4); 539-42.

Katoh N, et al Clin Exp Immunol. 2002 127:283-8.

Tsavellas G, et al Br J Surg. Oct. 2001; 88 (10) 1307-20.

Liefers GJ, et al Histopathology. May 1999; 34 (5):385-90.

Lacroix J, et al Sem Surg Oncol. 2001; 20:252-64.

Calaluce R, et al J. Sug Oncol. 1998; 67:194-202.

Ishida H, et al. Surg Today. 2003; 33 (12) 885-92.

Oberg A, et al. Anticancer Res. Mar.-Apr. 2000; 20 (2B) 1085-91.

Holter-Andersen, Mads N. et al "Plasma levels of Tissue Inhibitor of Metalloproteinases 1 measured during follow up of colorectal cancer patients have clinical value in predicting patient outcome," Proceedings of the American Association for Cancer Research Annual, vol. 43, Mar. 2002, p. 715.

Takada N. et al "Postoperative sequential changes of serum levels of matrix metalloproteinase and tissue inhibitor of metalloproteinase in Japanese patients with the squamous cell carcinoma of esophagus," Proceedings of the American Association for Cancer Research Annual, vol. 40, Mar. 1999, p. 346.

Zhou, W. et al "Identifying markers for pancreatic cancer by gene expression analysis," Database Medline [Online], Abstract of Cancer Epidemiology, Biomarkers & Prevention: A publication of the American Association for Cancer Research, Cosponsored by the American Society of Preventive Oncology, Feb. 1998, vol. 7, No. 2, 109-112, 2 pages.

National Library of Medicine, PubMed Website: "Serum levels of a tissue inhibitor of metalloproteinases-1 (TIMP-1) in bladder cancer patients", Naruo S et al., Int J Urol, vol. 1 No. 3 Sep. 1994, pp. 238-231.

National Library of Medicine, PubMed Website: "Tissue inhibitors of metalloproteinases (TIMP) in invasion and proliferation", Henriet P et al, APMIS, vol. 109, No. 1 Jan. 1999, pp. 111-119.

Dialog Information Services, File t59, Cancerlit, acession No. 93691448, Guillem JG et al., "Evaluation of tissue inhibitor of metalloproteinase-1 (TIMP-1) as a prognostic marker of human colorectal cancer invation", Proc Annu Meet Am Assoc Cancer Res: 34:A466 1993.

Dialog Information Services File 15, Cancerlit, accession No. 96647008, "Elevated tissue inhibitor of metalloproteinase 1 RNA in colorectal cancer stroma correlates with lymph node and distant metastases" Clin Cancer Res; 1 (8): 899-906 1995 Zeng Z et al.

Wood, et al "In Situ Hybridization Studies of Metalloproteinases 2 and 9 and TIMP-1 and TIMP-2 Expression in Human Prostate Cancer," Clinical & Experimental Metastasis (1997), 15 (3), 246-258.

Jung et al "Quantification of Matrix Metalloproteinases and Tissue Inhibitors of Metalloproteinase in Prostatic Tissue; Analytical Aspects", Prostate (1998) 34 (2), 130-136 New York.

Kjeldsen et al "Subcellular Localization and Release of Human Neutrophil Gelatinase, Confirming the Existence of Separate Gelatinase-containing Granules," Biochem J. 287:603-610 (1992).

Zeng ZS. et al High Levels of tissue inhibitor of metalloproteinase-1 (TIMP 1) in colorectal cancer, as determined by enzyme-linked immunosorbent assay (ELISA), correlate with poor outcome; proceedings of the American Association for Cancer Research, vol. 39; p. 298; Mar. 1998.

Foekens et al, J Natl. Cancer Inst., May 17, 1995 87(10):751-756 Urokinase-Type Plasminogen Activator and Its Inhibitor PAI-1: Predictors of Poor Response to Tamoxifen Therapy in Recurren Breast Cancer.

Harbeck et al Cancer Res. Aug. 15. 2002; 62(16):4617-22 Enhanced benefit from adjuvant chemotherapy in breast cancer patients classified high-risk according to urokinase-type plasminogen activator (uPA) and plasminogen activator inhibitor type 1 (n=3424).

Tanner et al: "Chromogenic in situ hybridization: a practical alternative for fluorescence in situ hybridization to detect HER-2/ neuoncogene amplification in archival breast cancer samples" Am J Pathol 157 (5): 1467-72, Nov. 2000.

Brunner N et al, Breast Cancer Res Treat, 24, 257-64; 1993.

Carmeliet et al., "Plasminogen activator inhibitor-1 gene-deficient mice. I. Generation by homologous recombination and characterization" Clin Invest. Dec. 1993; 92(6):2746-55,1993.

Carmeliet P. et al "Plasminogen activator inhibitor-1 gene-deficient mice. II. Effects on hemostasis, thrombosis, and thrombolysis" Clin Invest Dec. 1993;92(6):2756-60.

Tybulewicz VL et al, Cell 65(7):1153-63, Neonatal lethality and lymphopenia in mice with a homozygous disruption of the c-abl protoncogene Jun. 1991.

Tracy Plampton et al. Development of an enzyme linked immunosorbent assay to measure total TIMP-I (Free TIMP-1 and TIMP1 in combination with matrix-metalloproteinases) and measurement of TIMP and CRP in serum Clinica Chemica Acta 1995 137-154.

Abstract of Vincent Leroy et al., "Circulating Matrix Metalloproteinases 1, 2, 9 and Their Inhibitors TIMP-1 and TIMP-2 as Serum Markers of Liver Fibrosis With Chronic Hepatitis C: Comparison with PIIINP and Hyaluronic Acid" American Journal of Gastroenterology, 2004 (pp. 271-279).

Abstract of Baker T, Tickle S, Wasan H, Docherty A, Isenberg D & Waxman J (1994) Serum metalloproteinases and their inhibitors: markers for malignant potential. *Br.J.Cancer* 70, 506-512.

Birkedal-Hansen H, Moore WG, Sodden MK, Windsor LJ, Birkedal-Hansen B, DeCarlo A & Engler JA (1993) Matrix metalloproteinases: a review. *Crit.Rev.Oral Biol.Med.* 4, 197-250.

Abstract of Clark IM, Powell LK, Wright JK & Cawston TE (1991) Polyclonal and monoclonal antibodies against human tissue inhibitor of metalloproteinases (TIMP) and the design of an enzyme-linked immunosorbent assay to measure TIMP. *Matrix* 11, 76-85.

Cooksley, S. et al., "Immunoassays for the Detection of Human Collagenase, Stromelysin, Tissue Inhibitor of Metalloproteinases (TIMP) and Enzyme-Inhibitor Complexes", Matrix, 10, pp. 285-291, 1990.

Cooper, TW et al., "Platelet-Derived Collagenase Inhibitor: Characterization and Subcellular Localization", Proc. Natl. Acad. Sci., USA, 82, pp. 2779-2783, May 1985.

DeClerk Ya, Perez N, Shimada H, Boone TC, Langley KE & Taylor SM (1992) "Inhibition of Invasion and metastasis in cells transfected with an inhibitor of metalloprotenases" Cancer Res. 52, 701-708 (1992).

Fujimoto N, Zhang J, Iwata K, Shinya T, Okada Y & Hayakawa T (1993) A one-step sandwich enzyme immunoassay for tissue inhibitor of metalloproteinases-2 using monoclonal antibodies. Clin.Chim. Acta 220, 31-45.

Goldberg, GI et al., "Interaction of 92-kDA Type IV Collagenase with the Tissue Inhibitor of Metalloproteinases Prevents Dimerization, Complex Formation with Interstitial Collagenase, and Activation of the Proenzyme with Stromelysin", J. Biol. Chem., 267(7), pp. 4583-4591, 1992.

Hembry RM et al., "Immunolocalization of Tissue Inhibitor of Metalloproteinases (TIMP) in Human Cells Characterization and Use of a Specific Antiserum", J. Cell Sci., 73, pp. 105-119, 1985.

Holten-Andersen, M. et al., "Total Levels of Tissue Inhibitor of Metalloproteinases 1 in Plasma Yield High Diagnostic Sensitivity and Specificity in Patients with Colon Cancer", Clin. Cancer Res., 8(1), pp. 156-164, Jan. 2002 Official Journal of the American Association for Canser Research.

Jung, K. et al., "What Kind of Specimen Should Be Selected for Determining Tissue Inhibitor of Metalloproteinase-1 (TIMP-1) in Bloiod?", Clin. Chim. Acta, 254, pp. 97-100, 1996.

Jung K, Nowak L, Lein M, Henke W, Schnorr D & Loening SA (1996) Role of specimen collection in preanalytical variation of metalloproteinases and their inhibitors in blood. Clin.Chem. 42, 2043-2045.

Abstract of Jung K, Nowak L, Lein M, Priem F, Schnorr D, Loening SA (1997) Matrix metalloproteinases 1 and 3, tissue inhibitor of metalloproteinase-1 and the complex of metalloproteinase-1/tissue inhibitor in plasma of patients with prostate cancer. Int. J. Cancer 74, 220-223.

Abstract of Keyszer G, Lambiri I, Nagel R, Keysser C, Keysser M, Gromnica-Ihle E, Franz J, Burmester GR, Jung K (1999) Circulating levels of matrix metalloproteinases MMP-3 and MMP-1, tissue inhibitor of metalloproteinases (TIMP-1), and MMP-1/TIMP-1 complex in rheumatic disease. Correlation with clinical activity of rheumatoid arthritis versus other surrogate markers. J. Rheum. 26, 251-258.

Abstract of Khokha R & Waterhouse P (1993) The role of tissue inhibitor of metalloproteinase-1 in specific aspects of cancer progression and reproduction. J.Neurooncol. 18, 123-127.

Khokha R, Zimmer MJ, Graham CH, Lala PK & Waterhouse P (1992a) Suppression of invasion by inducible expression of tissue inhibitor of metalloproteinase-1 (TIMP-1) in B16-F10 melanoma cells. J.Natl.Cancer Inst. 84, 1017-1022.

Abstract of Khokha R, Zimmer MJ, Wilson SM & Chambers AF (1992b) Up-regulation of TIMP-1 expression in B16-F10 melanoma cells suppresses their metastatic ability in chick embryo. Clin.Exp. Metastasis 10, 365-370.

Kleiner Jr DE, Tuuttila A, Tryggvason K & Stetler-Stevenson WG (1993) Stability analysis of latent and active 72-kDa type IV collagenase: the role of tissue inhibitor of metalloproteinases-2 (TIMP-2). Biochemistry 32, 1583-1592.

Abstract of Kodama S, Yamashita K, Kishi J, Iwata K & Hayakawa T (1989) A sandwich enzyme immunoassay for collagenase inhibitor using monoclonal antibodies. Matrix 9, 1-6.

Liotta et al., "Cancer Metastasis and Angiogenesis: An Imbalance of Positive and Negative Regulation", Cell, p. 64, 327-36, 1991.

Abstract of McDougall JR & Matrisian LM (1995) Contributions of tumor and stromal matrix metalloproteinases to tumor progression, invasion and metastasis. Cancer Metastasis Rev. 14, 351-362.

Abstract of Matrisian LM (1992) The matrix-degrading metalloproteinases. Bioessays 14, 455-463.

Abstract of Mimori K, Mori M, Shiraishi T, Fujie T, Baba K, Haraguchi M, Abe R, Ueo H & Akiyoshi T (1997) Clinical significance of tissue inhibitor of metalloproteinase expression in gastric carcinoma. Br.J.Cancer 76, 531-536.

Moll UM, Youngleib GL, Rosinski KB & Quigley JP (1990) Tumor promoter-stimulated Mr 92,000 gelatinase secreted by normal and malignant human cells: isolation and characterization of the enzyme from HT1080 tumor cells. Cancer Res. 50, 6162-6170.

Abstract of Moutsiakis D, Mancuso P, Krutzsch H, Stetler-Stevenson WG & Zucker S (1992) Characterization of metalloproteinases and tissue inhibitors of metalloproteinase's in human plasma. Connect. Tissue Res. 28, 213-230.

Murphy et al , "The N-Terminal Domain of Tissue Inhibitor of Metalloproteinase Retains Metalloproteinsase Inhibitor Activity," Biochemistry 30:8097-8102 (1991).

Murphy G, Houbrechts A, Cockett MI, Williamson RA, O'Shea M & Docherty AJ (1991) The N-terminal domain of tissue inhibitor of metalloproteinases retains metalloproteinase inhibitory activity [published erratum appears in Biochemistry Oct. 22, 1991; 30(42):10362]. Biochemistry 30, 8097-8102.

Stetler-Stevenson WG, Hewitt R & Corcoran M (1996) Matrix metalloproteinases and tumor invasion: from correlation and causality to the clinic. Semin.Cancer Biol. 7, 147-154.

Stetler-Stevenson WG, Krutzsch HC & Liotta LA (1989) Tissue inhibitor of metalloproteinase (TIMP-2). A new member of the metalloproteinase inhibitor family. J.Biol.Chem. 264, 17374-17378.

Stetler-Stevenson WG, Liotta LA & Kleiner Jr DE (1993) Extracellular matrix 6: role of matrix metalloproteinases in tumor invasion and metastasis. FASEB J. 7, 1434-1441.

Thorgeirsson UP, Lindsay CK, Cottam DW & Gomez DE (1993) Tumor invasion, proteolysis, and angiogenesis. J.Neurooncol. 18, 89-103.

Welgus HG, Jeffrey JJ, Eisen AZ, Roswit WT & Stricklin GP (1985) Human skin fibroblast collagenase: interaction with substrate and inhibitor. Coll.Relat.Res. 5, 167-179.

Wilhelm SM, Collier IE, Marmer BL, Eisen AZ, Grant GA & Goldberg GI (1989) SV40-transformed human lung fibroblasts secrete a 92-kDa type IV collagenase which is identical to that secreted by normal human macrophages [published erratum appears in J Biol Chem Dec. 25, 1990; 265(36):22570].J.Biol.Chem. 264, 17213-17221.

Zucker S, Lysik RM, DiMassimo BI, Zarrabi HM, Moll UM, Grimson R, Tickle SP & Docherty AJ (1995) Plasma assay of gelatinase B: tissue inhibitor of metalloproteinase complexes in cancer. Cancer 76, 4,1995 700-708.

Holten-Andersen, MN, et al, 2000, High preoperative plasma tissue inhibitor of metalloproteinase-1 levels are associated with short survival of patients with colorectal cancer, Clinical Cancer Research, vol. 6, No. 11, pp. 4292-4299.

Michael, M, et al, 1999, Expression and prognostic significance of metalloproteinases and their tissue inhibitors in patients with small-cell lung cancer, Journal of Clinical Oncology, vol. 17, No. 6, pp. 1802-1808.

Pohl, AL, et al, 1994, Neural network evaluation of multiple tumor markers for diagnosis of ovarian cancer (meeting abstract), Non-serial, 3.sup.rd International Conference of the Mediterranean Society of Tumor Marker Oncology, CANCERLIT Accession No. 95614997.

Garrett c. Durkan et al "Prognostic Significance of Matrix Metalloproteinase-1 and Tissue Inhibitor of Metalloproteinase-1 in Voided Urine Samples with Patients with Transitional Cell Carcinoma of the Bladder", Clinical Cancer Research, vol. 7, Nov. 2001, pp. 3450-3456, XP 002268767.

Holten-Andersen et al., "Quantitation of TIMP-1 in Plasma of Healthy Blood Donors and Patients with Advanced Cancer," British Journal of Cancer 80:495-503 (1999).

Ward, AM, 1985, Tumour Markers, Developmental Oncology, vol. 21, pp. 90-106.

Genesis Group Associates, Inc., 1997, New tests improve breast cancer prognosis, Genesis Report-Dx, vol. 6, No. 3, NLDB Accession No. 97:320100.

Berend, KR, et al, 1998, Association between ratio of matrix metalloproteinase-1 to tissue inhibitor of metalloproteinase-1 and local recurrence, metastasis, and survival, Journal of Bone and Joint Surgery, American Volume, vol. 80, No. 1, pp. 11-17.

Ikebe, T, et al, 1999, Gelatinolytic activity of matrix metalloproteinase in tumor tissues correlates with the invasiveness of oral cancer, Clinical and Experimental Metastasis, vol. 17, No. 4, p. 315-323.

Arnold, SM, et al, 1999, Expression of p53, bcl-2, E-cadherin, matrix metalloproteinase-9, and tissue inhibitor of metalloproteinase-1 in paired primary tumors and brain metastases, Clinical Cancer Research, vol. 5, No. 12, pp. 4028-4033.

McKay, JA, et al, 2000, Application of the enrichment approach to identify putative markers of response to 5-fluorouracil therapy in advanced colorectal carcinomas, International Journal of Oncology, vol. 17, No. 1, pp. 153-158.

Aoudjit, F, et al, 1999, Gelatinase B (MMP.sub.--9), but not its inhibitor (TIMP-1), dictates the growth rate of experimental thymic lymphoma, International Journal of Cancer, vol. 82, No. 5, pp. 743-747.

Tockman, MS, et al, 1992, Considerations in bringing a cancer biomarker to clinical application, Cancer Research, vol. 52, Suppl., pp. 2711s-2718s.

Plumpton TA, et al. Clinica Chemica Acta. 1995; 240: 137-54.

Mads N. Holten-Andersen et al., "Measurement of the Noncomplexed Free Fraction of Tissue Inhibitor of Metalloproteinases 1 in Plasma by Immunoassay", Clinical Chemistry 48:8, 1305-1313 (2002).

Agency for Health Care Policy and Research, "Colorectal Cancer Screening: Summary", Evidence Report: No. 1. AHCPR Publ. No. 97-0302, pp. 1-4, May 1998.

Aznavoorian S. et al., "Molecular Aspects of Tumor Cell Invasion and Metastasis" Cancer, 15, 71(4), pp. 1368-1383, 1993.

Balk, S.P. et al., "Biology of Neoplasia, Biology of Prostate-Specific Antigen", Journal of Clinical Oncology, 21(2), pp. 383-391, 2003.

Benson, A.B. et al., "ASCO Special Article—2000 Update of American Society Colorectal Cancer Surveillance Guidelines", Journal of Clinical Oncology, 18(20), pp. 3586-3588, Oct. 15, 2000.

Birkedal-Hansen, "Role of Matrix Metalloproteinases in Human Periodontal Diseases", J. Periodontol., pp. 474-484, May 1993.

Breimer, D.D. et al., "Saliva: A Fluid for Measuring Drug Concentrations", Pharmacy Internation, 1, pp. 9-11, 1980.

Khokha, R. et al., "AntisenseRNA-Induced Reduction in Murine TIMP Levels Confers Oncogenicity on Swiss 3T3 Cells", Science, 243, pp. 947-950, Feb. 17, 1989.

Lovgren J., et al "Measurement of Prostate-Specific Antigen and Human Glandular Kallikrein 2 in Different Body Fluids", J. Androglogy, 20, pp. 348-355,1999.

Remacle, A. et al., "High Levels of TIMP-2 Correlate with Adverse Prognosis in Breast Cancer", Int. J. Cancer, 89, pp. 118-121, 2000.

Turan T. et al., "Free and Total Prostate-Specific Antigen Levels in Saliva and the Comparison with Serum Levels in Men", Eur. Urol., 38(5), pp. 550-554, 2000.

Vignola et al., "Sputum Metalloproteinase-9/Tissue Inhibitor of Metalloproteinase-1 Ratio Correlates with Airflow Obstruction in Asthma and Chronic Bronchitis", Am. J. Respir. Crit. Care Med., 158, pp. 1945-1950, 1998.

Vining, R. and McGinley, RA, "Hormones in Saliva", Critical Reviews in Clinical Laboratory Science, 23, pp. 95-146, 1985.

Wolff, K. et al., Hay A., "Methadone in Saliva", Clinical Chemistry, 37, pp. 1297-1298, 1991.

McCarthy K. et al., "High Levels of Tissue Inhibitor of Metalloproteinase-1 Predict Poor Outcome in Patients with Breast Cancer", Int. J. Cancer, 84, pp. 44-48, 1999.

International Search Report PCT/DK2003/000634, Feb. 2, 2004.
International Search Report PCT/DK2005/00218, Aug. 2, 2005.
European Patent Office Search Report DKA 200400506, Mar. 2, 2005.

* cited by examiner

ELISA OF HUMAN MMP-9:TIMP-1 IN PLASMA

ELISA OF FREE (NON-COMPLEXED) HUMAN TIMP-1 IN PLASMA

TISSUE INHIBITOR OF MATRIX METALLOPROTEINASES TYPE-1 (TIMP-1) AS A CANCER MARKER

This application is a divisional of U.S. patent application Ser. No. 09/546,573, filed Apr. 10, 2000, which claims benefit of Denmark PA 1999 00476, filed Apr. 9, 1999, both of which are incorporated herein by reference.

BRIEF DESCRIPTION OF THE INVENTION

The present invention relates to a test to be used to screen large populations for the occurrence of cancer. The method is based on the measurement of tissue inhibitor of metalloproteinases 1 (TIMP-1) in body fluids. The invention permits the early identification of patients having colorectal cancer. The method is highly specific, and patients with non-malignant conditions, such as inflammatory bowel diseases, are not detected. Measurement of another similar inhibitor, TIMP-2, does not demonstrate equivalent clinical value, indicating an additional level of specificity of the invention.

The test is based on the measurement of tissue inhibitor of metalloproteinases type 1 (TIMP-1), in various body-fluids, including plasma,: serum, stool and urine TIMP-1 concentrations can be determined either as the total TIMP-1 concentration, the free TIMP-1 concentration, the concentration of complexes between TIMP-1 and MMP's and/or ratios and fractions thereof, hereafter referred to as TIMP-1 levels. According to the invention, individuals with a high likelihood of having cancer, e.g. colon cancer, can be identified by elevated TIMP-1 levels in their body fluids, while individuals with low TIMP-1 levels are unlikely to suffer from cancer, e.g. colon cancer. Thus, the invention can be used to identify individuals with a high probability of having early stage, non-symptomatic cancer, e.g. colon cancer. The identified individuals should be further examined and if cancer is found, the patients should be offered surgery, irradiation, and/or adjuvant anti-neoplastic therapy, thereby increasing the chance of cure of cancer for the individual.

BACKGROUND

Colorectal cancer is the fourth most frequent cancer in the Western world, with about 130,000 new cases yearly in the US. Forty to 50% of all colorectal cancer patients will be diagnosed with early stage disease (Dukes' stage A or B). Most of these patients with early stage colorectal cancer can be cured by surgery alone. Thus, risk of recurrence is closely related to stage of disease at time of primary surgery, with about a 10% relapse rate in Dukes' stage A and 25-30% in Dukes' stage B. Patients with Dukes' stage C colorectal cancer have a five-year relapse rate of 70% following surgery and are offered adjuvant chemotherapy. Following relapse, the risk of dying of the disease is significant. Thus, one way to improve survival is to increase the number of patients being diagnosed with early stage disease. Screening for colorectal cancer has been shown to improve survival, however, current tests suffer from a lack of compliance, from low sensitivity, and from the need for strict dietary restrictions. Thus, the development of, new and improved tests for the early detection of colorectal cancer is needed.

Because metastatic disease is the main cause of cancer patient morbidity and mortality, molecules involved in the regulation of tumor invasion and metastasis are attractive as potential diagnostic/prognostic targets. It is well established that proteolytic enzymes produced by cancer cells or by cells in the tumor stroma are involved in extracellular tissue degradation, leading to cancer cell invasion and metastasis. A number of enzymes have been associated with this process, the most thoroughly investigated, being the metalloproteinases, such as the collagenases and stromelysins, and the serine proteases such as plasmin. Recently, data have been published indicating that these molecules, free or bound in complexes, are released from tumor tissue and find their way into the circulation.

Matrix metalloproteinases (MMP's) play a pivotal role in cancer growth and spread, contributing to enzymatic degradation of the extracellular matrix (Liotta et al, 1991; Stetler-Stevenson et al, 1993; MacDougall & Matrisian, 1995). The naturally occurring inhibitors of MMP's, tissue inhibitors of MMP's (TIMP's), form tight 1:1 stoichiometric complexes with the activated forms of the MMP's (Welgus et al, 1985; Kleiner et al, 1993), thereby inhibiting the catalytic activity of these enzymes (Stetler-Stevenson et al, 1996; Goldberg et al, 1992; Birkedal-Hansen et al, 1993). While the balance between the matrix-degrading properties of MMP's and the inhibitory effect of TIMP's is closely regulated under normal physiological conditions (Matrisian, 1992; Thorgeirsson et al, 1993; Birkedal-Hansen et al, 1993), this balance might be disrupted in malignant tissue.

A number of enzyme-linked immunoassays for the detection of TIMP-1 (Kodama et al, 1989; Cooksley et al, 1990; Clark et al, 1991) and TIMP-2 (Fujimoto et al, 1993) have been described. These assays have been applied to body fluids, e.g. serum, plasma, amniotic fluid, cerebrospinal fluid, urine, but the number of samples tested has not been sufficient to establish normal ranges for TIMP levels in healthy individuals (Kodama et al, 1989; Clark et al, 1991). Furthermore, none of these assays has been sufficiently validated for technical performance or for clinical use.

In a study by Mimori et al (Mimori et al, 1997) in which tumor tissue levels of TIMP-1 mRNA were studied in patients with gastric carcinoma, high tumor/normal tissue ratios of TIMP-1 mRNA were found to be associated with increased invasion and poor prognosis. However, TIMP-1 protein levels in, sera from prostate-cancer patients and healthy donors (Baker et al, 1994) showed a high degree of overlap. Similarly, a separate study of plasma from prostate cancer patients and healthy donors showed no difference in TIMP-1 levels between the two groups (Jung et al, 1997).

Studies of TIMP-1 complexed with MMP-9 in plasma of patients with advanced gastrointestinal and gynaecological cancer (Zucker et al, 1995) demonstrated significantly higher levels in blood samples from cancer patients with metastatic disease compared to healthy control individuals, and that patients with high levels of TIMP-1:MMP-9 complex had a shorter survival (Zucker et al, 1995 and U.S. Pat. No. 5,324, 634). However, this study did not include measurements of total or free TIMP-1, only the complex between TIMP-1 and one of the up to now approximately 24 identified MMP's. Furthermore, in this study, no differences in complex levels were found between patients with breast cancer and healthy donors. Also, this study did not include patients with early stage cancer.

DETAILED DESCRIPTION OF THE INVENTION

In a number of cancer types, there is a critical and unmet need for highly sensitive and specific markers for screening large populations for the presence of malignant disease. Such markers should be able to identify individuals with a high probability of early stage cancer. These individuals should be further examined, and if cancer is found, they should subsequently be offered surgery, radiation, or adjuvant anti-neoplastic therapy.

Since proteinases and their receptors and inhibitors seem to play a pivotal role in the basic mechanisms leading to cancer invasion, these molecules may be expressed at a very early time point in the carcinogenic process. As many of these molecules exert their biological action extracellularly, they may be present at elevated levels in body fluids, even in patients with early stage invasive malignant disease. Moreover, since these molecules are involved in the more basic features of malignant progression, e.g. invasion and metastasis, it should be investigated which forms of cancer that display an increase in these molecules.

The present invention relates to a method to aid in the diagnosis of colorectal cancer in a patient, said method comprising determining the amount of total, complexed and/or free TIMP-1 levels and ratios and fractions thereof in body fluids such as blood, serum, plasma, urine, faeces or cerebrospinal fluid.

An aspect of the present invention relates to a method for determining whether an individual is likely to have cancer, the method comprising determining a first parameter representing the concentration of TIMP-1 in body fluid samples, and indicating the individual as having a high likelihood of having cancer if the parameter is at or beyond a discriminating value and indicating the individual as unlikely of having cancer if the parameter is not at or beyond the discriminating value.

The first parameter may be obtained by combining the concentration of total TIMP-1 with the concentration of free TIMP-1. The combination may be performed by logistic regression analysis.

In an aspect of the invention, at least one second parameter is additionally determined, which represents the concentration of an additional marker different from any form of TIMP-1, in a body fluid sample from the individual. The first parameter representing the concentration of TIMP-1 in a body fluid sample of an individual and the at least one second parameter (different from any form of TIMP-1 in the individual's body fluid sample) may be combined to produce a combined parameter. If the combined parameter is at or beyond a discriminating value, the individual is indicated as having a high likelihood of having cancer. If the combined parameter is not at or beyond the discriminating value, the individual is unlikely to have cancer. In this embodiment, the discriminating value of the combined parameter is a value determined by determining the combined parameter in both a healthy control population and a population with known cancer. Thus, the discriminating value identifies the cancer population with a predetermined specificity or a predetermined sensitivity.

The at least one second parameter may be a parameter representing the concentration of a tumour marker. Such tumour marker may be selected from the group consisting of CEA, soluble u-PAR, cathepsin B, HER2-neu, CA 15-3 and YKL-40.

The combining to generate any combined parameter may be performed by logistic regression analysis.

The method of the invention can be applied to various cancers, such as colorectal cancers and metastatic breast cancer (i.e., breast cancer in patients who have been previously treated for breast cancer). In one embodiment directed to screening an individual for metastatic breast cancer, the determination of the appropriate parameter is performed at several points in time at intervals, as part of monitoring of a cancer patient after the treatment for primary cancer.

The parameter representing the concentration of TIMP-1 may be the concentration proper of TIMP-1. TIMP-1 exists both in free form and in the form of complexes with metalloproteinases, and it has been found that an important parameter is, the total concentration of TIMP-1, that is, the sum of the TIMP-1 in free form and the TIMP-1 in complex forms. It will be understood that the other expressions than the concentration proper can represent the concentration, such as, e.g., the concentration multiplied by a factor, etc. etc., and that such other representations can be used equally well for the purpose of the present invention provided the corresponding adjustments are made.

The discriminating value is a value which has been determined by measuring the parameter in both a healthy control population and a population with known cancer thereby determining the discriminating value which identifies the cancer population with either a predetermined specificity or a predetermined sensitivity based on an analysis of the relation between the parameter values and the known clinical data of the healthy control population and the cancer patient population, such as it is apparent from the detailed discussion in the examples herein. The discriminating value determined in this manner is valid for the same experimental setup in future individual tests.

Specificity is defined as the proportion of non-diseased individuals that are correctly identified by the described method of the invention. Sensitivity is defined as the proportion of diseased individuals that are correctly identified by the described method.

The invention may be used both for an individual and for an entire population.

In the specific experimental setups described herein, the concentration threshold of total TIMP-1 useful as a discriminating value was found to be in the range of 50-160 microgram/L of total TIMP-1 at a specificity of 90%. Other experimental setups and other parameters will result in other values which can be determined in accordance with the teachings herein.

The method can be applied to an unselected population, but more appropriately to a population already identified as having an increased risk of developing cancer, e.g. individuals with a genetic disposition, individuals who have been exposed to carcinogenic substances, or individuals with cancer-predisposing non-malignant diseases. In the case of colorectal cancer, the population selected for the invention could represent individuals with a prior polyp, individuals with Crohn's disease or ulcerative colitis, individuals with one or more family members with colorectal cancer, or individuals with a prior resection of an early colorectal cancer.

When an individual has been identified as having high TIMP-1 levels in his or her body fluid, the individual should be referred for further examination. If a cancer is found, the patient could be offered surgery, radiation or adjuvant antineoplastic therapy aiming at curing the patient of cancer.

Example 1 describes the preparation and validation of an assay that measures total TIMP-1 with high analytical sensitivity and specificity. It is described that healthy blood donors have a very narrow range of plasma total TIMP-1.

In Example 2, the formatting of a TIMP-1:MMP-9 ELISA is described. The format, execution, and validation of this assay are similar to those for total TIMP-1, except that a polyclonal antibody against MMP-9 is used in the capture step. By substituting the MMP-9 antibody with an antibody against another MMP, complexes between TIMP-1 and other MMP's can be quantitated.

In Example 3, the formatting of a TIMP-1 assay which exclusively measures free TIMP-1, is described. This assay utilizes a monoclonal anti-TIMP-1 antibody (MAC 19) which only recognises TIMP-1 in its uncomplexed form.

Thus, this assay will measure the amount of free TIMP-1 in a sample. The execution, and validation of this assay are similar to the assay for total TIMP-1

By subtracting the free TIMP-1 concentration from the total TIMP-1 concentration in a biological sample, the concentration of all complexed forms of TIMP-1 can be determined. It should be emphasized that TIMP-1 can form complexes with many of the MMP's and therefore, subtracting one type of complex from the total amount of TIMP-1 will only provide information on the fraction of TIMP-1 not being complexed to this specific MMP.

Figure 13:
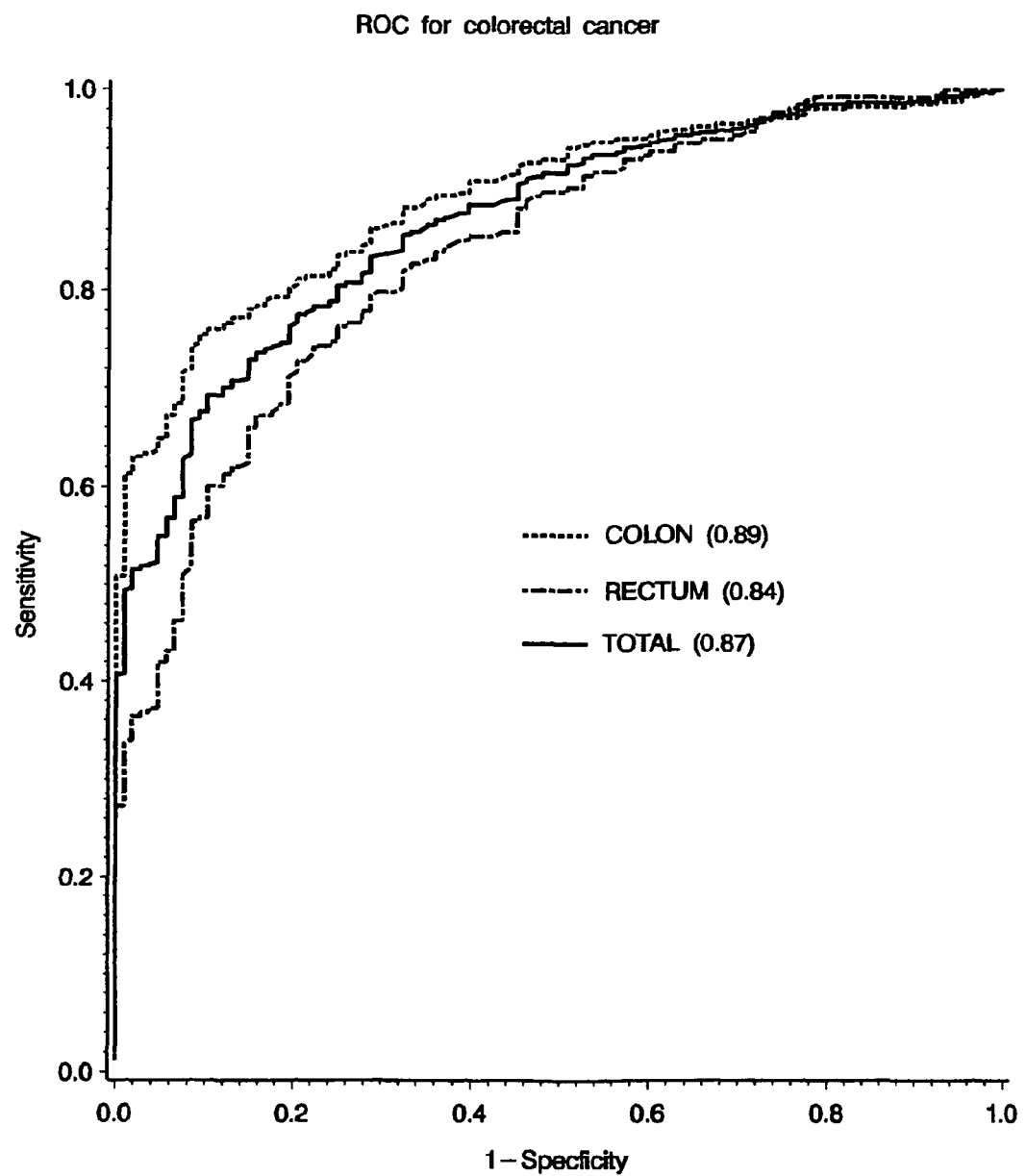

In Example 4, which includes data regarding plasma TIMP-1 levels from healthy blood donors and from patients with known colorectal cancer, it is shown that patients suffering from colorectal cancer have significantly elevated total TIMP-1 levels in their preoperative plasma samples. A percentile plot of the total TIMP-1 levels in plasma from all colorectal cancer patients and from healthy blood donors shows that a total TIMP-1 concentration of 119.1 pg/L is the $90^{th}$ centile of the healthy donors. Using this cut-off, 68% of the colorectal cancer patients were identified as having elevated plasma TIMP-1 levels. When analyzing the colon cancer patients separately, it was shown that total TIMP-1 measurements in plasma identified 75% of the colon cancer patients (sensitivity) with a 90% specificity (10% of the healthy blood donors were classified as being high). Similarly, it was shown for the rectal cancer patients, that total TIMP-1 measurements in plasma identified 60% of the rectal cancer patients with a 90% specificity. If a higher or lower sensitivity or specificity is desired, the cut-off value can be changed. This is illustrated in FIG. 13 showing ROC curves of total TIMP-1 in plasma from colorectal cancer patients. In addition, ROC curves are included for the individual groups of colon and rectal cancer patients. Any other information which can be derived from these ROC curves falls within the scope of the present invention.

Figure 15:
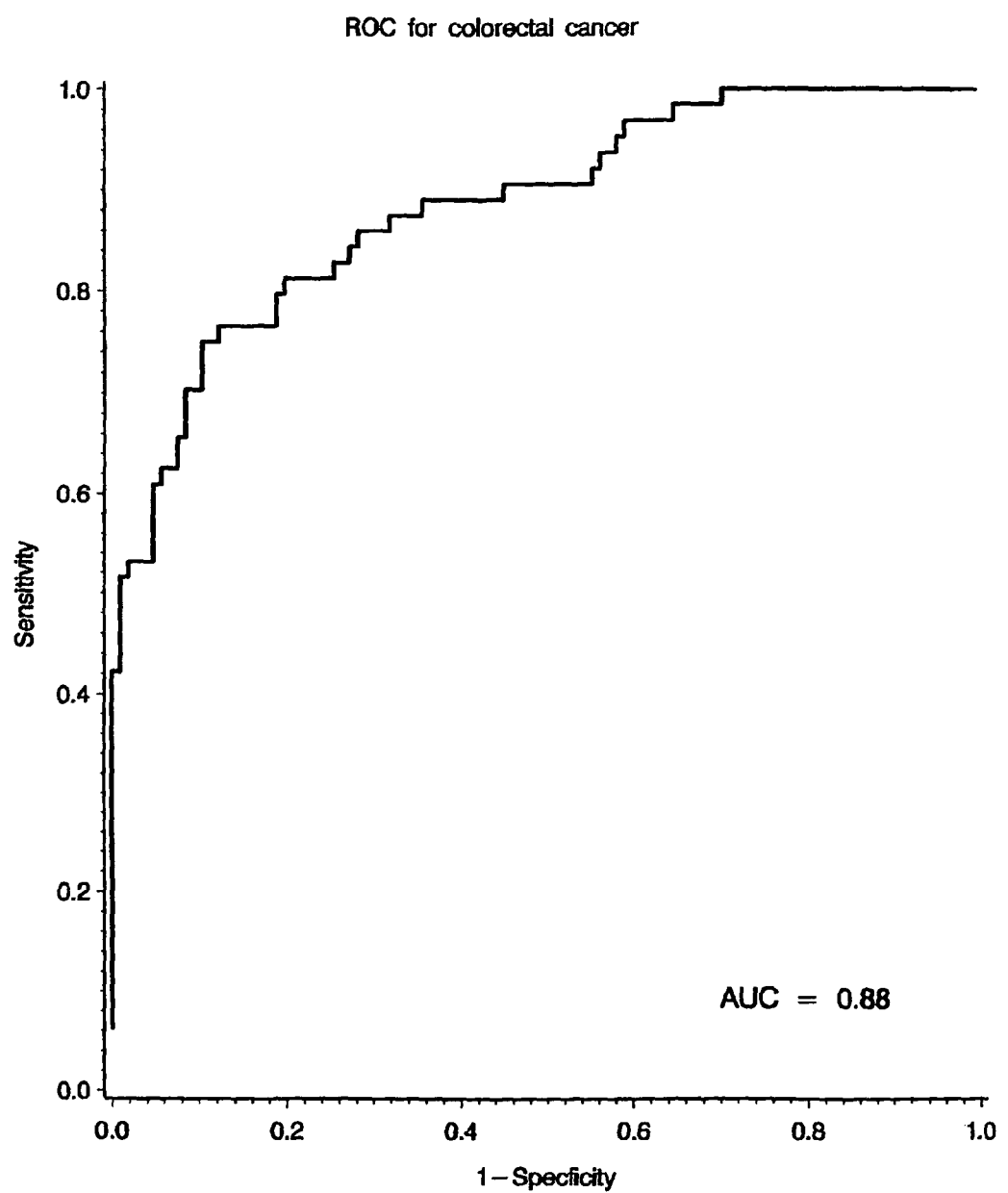

An independent prospective study, including preoperative plasma samples from 64 patients with colon (n=43) or rectal (n=21) cancer confirmed the data obtained from the above described study (FIG. 15). An additional study of 180 healthy blood donors and 20 colorectal cancer patients, using different antibodies (Anti TIMP-1 11 E/C6, Anti-TIMP-1 RRU-T6) in an automated immunoassay, further corroborated the previous clinical results. Moreover, the absolute values generated from the automated assay showed a high degree of correlation to those obtained by the assay described in Example 1 (r=0.9).

The clinical value of a marker for cancer detection or screening is related to its ability to detect early stages of disease, potentially impacting survival. It was shown that total TIMP-1 was as efficient in detecting or screening early stage colorectal cancer (Dukes' stages A and B) as it was in the total population of colorectal cancer patients (FIG. 14), Thus, detection or screening with total TIMP-1 will result in more patients being diagnosed with early stage cancer. In a similar manner, any information that can be derived from FIG. 14 falls within the scope of the present invention.

Figure 14:
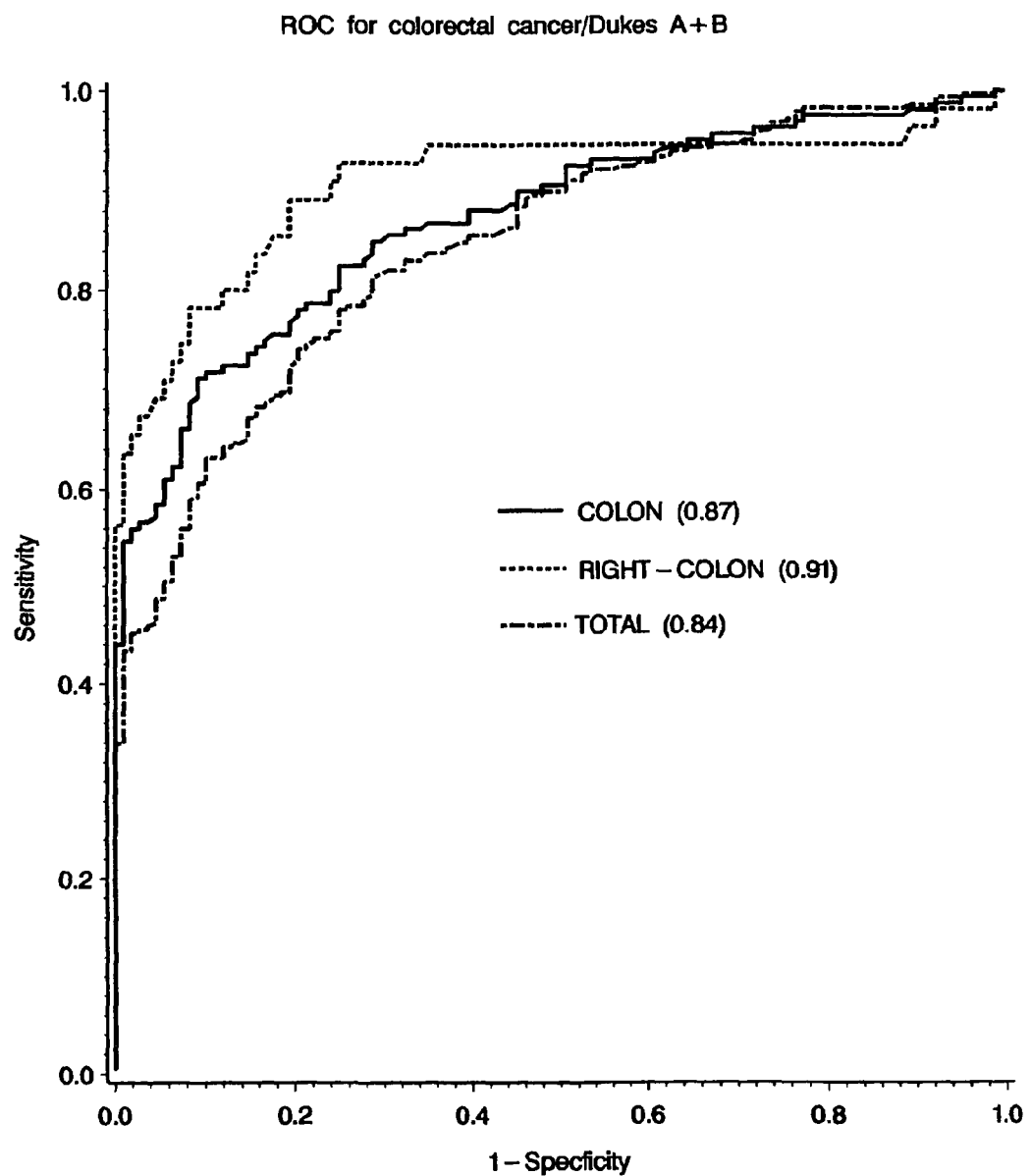

By dividing the colon cancer patients into two groups, patients with left-sided and right-sided tumors respectively, it was evident that measurement of total TIMP-1 was especially useful in identifying those patients with early stage, right-sided colon cancer lesions (FIG. 14).

The specificity of a given cancer detection or screening test is based on the efficiency of the test to identify only those patients suffering from cancer while patients suffering from non-malignant diseases should not be identified as false positive subjects. In the case of colorectal cancer, it is important that the test in question can distinguish between malignant and non-malignant diseases of the colon and rectal. This is particularly important for diseases like Crohn's disease and ulcerative colitis, since patients with these diseases are at higher risk of developing cancer.

In Example 5 it is shown that total TIMP-1 levels are significantly higher in patients with colorectal cancer than in patients with inflammatory bowel diseases (IBD), showing that total TIMP-1 can be used to detect or screen colorectal cancer in a population of patients with IBD. That TIMP-1 is not increased in non-malignant diseases is supported by a recent paper, (Keyser et al, 1999), demonstrating that patients with rheumatoid arthritis do not have increased plasma TIMP-1 levels. Also, by comparing total TIMP-1 levels among patients with IBD (excluding patients with clinically assessed acute active disease, n=4) and healthy blood donors, no significant differences in total plasma TIMP-1 levels were found (p=0.56), showing that these non-malignant diseases do not give false positive test results.

In Example 6, the additive effect of the measurement of an additional colorectal cancer marker is described. Carcino Embryonic Antigen (CEA) was measured in all cancer patient and healthy blood donor samples. Combining CEA and the TIMP-1 levels measured by the assay described in Example 1, it could be shown that while CEA alone gives 35% sensitivity at a 98% specificity, the sensitivity of the combination of CEA and total TIMP-1 as determined by logistic regression analysis increased to 57%, without sacrificing specificity.

In Example 7 it is shown that patients suffering from colorectal cancer have significantly elevated free TIMP-1 levels in their preoperative plasma samples. A percentile plot including the free TIMP-1 levels from the colorectal cancer patients as well as free TIMP-1 levels from healthy blood donors, showed that colorectal cancer patients had significantly elevated free TIMP-1 levels as compared to blood donors p=0.02. A ROC curve was created (FIG. 18) for these patients and donors and it was seen that free TIMP-1 gave an area under the curve (AUC) of 0.61.

In Example 8, the use of the TIMP-1:MMP-9 complex assay as an aid for the diagnosis of colorectal cancer is described.

TIMP-1 is known to exist either as the free molecule or in complex with MMP's, preferentially MMP-9. Measuring total TIMP-1, complexed TIMP-1 and free TIMP-1 will make it possible to validate each of these species for their potential detection or screening value. In addition, it will be possible to calculate ratios or any derived algorithm between the different species which might provide additional detection or screening value.

In Example 9, the detection or screening value of the combination of total and free TIMP-1 is described.

The data shows that combining by logistic regression analysis the free TIMP-1 measurements with the total TIMP-1 measurements, a significant increase in the AUC was demonstrated. Any information that can be derived from FIG. 18 falls within the scope of the present invention.

The specificity of a given cancer screening test is based on the efficacy of the test to identify only those patients suffering from cancer while patients suffering from non-malignant diseases should not be identified as false positive. However, it would be desirable that the test was specific for a specific type of cancer, e.g. colon cancer, instead of being a pan-cancer marker.

In Example 10, total plasma TIMP-1 values in preoperative blood samples from a cohort of 322 patients with primary breast cancer (stage 1 and 11) as compared with total TIMP-1 levels in 108 healthy blood donors are described. It was shown that the breast patients had a median, total TIMP-1 level of 88.3 µg/L, while the healthy donors had a median plasma concentration of total TIMP-1 of 88.9 µg/L. The difference between these values is not clinically significant, supporting the specificity of TIMP-1 levels for the detection or screening of colorectal cancer. However, it should be studied whether elevated plasma TIMP-1 levels are found in patients with early stage non-colorectal cancer.

In Example 11, total TIMP-1 levels in patients with metastatic breast cancer are described.

Of note, total TIMP-1 in plasma from women with metastatic breast cancer had a median value of 236 µg/L, significantly higher than levels in healthy blood donors. This shows the potential of using plasma TIMP-1 levels for the management of breast cancer patients.

In Example 12, the concentrations of TIMP-2 in preoperative plasma samples from patients with colorectal cancer are described.

TIMP-2 is another tissue inhibitor of metalloproteinases with a high degree of homology to TIMP-1. Using a specific immunoassay for TIMP-2, concentrations of this inhibitor were determined in plasma samples from colorectal cancer patients and in healthy blood donors. No significant differences in plasma TIMP-2 levels were found between the two populations, supporting the unique value of TIMP-1 as an aid for the early detection or screening of colorectal cancer.

FIGURE LEGENDS

FIG. 1: Kinetic assay for TIMP-1. Progress curves for the change in absorbance at 405 nm produced by hydrolysis of p-nitrophenyl phosphate by solid-phase bound alkaline phosphatase immunoconjugate The data shown are generated by 4 individual assay wells treated with 4 different concentrations of purified recombinant TIMP-1; 10 µg/L ($\nabla$-$\nabla$), 2.5 µg/L ($\Delta$-$\Delta$), 0.63 µg/L ($\square$-$\square$) and 0.16 µg/L (O-O). The lines shown have been fitted by simple linear regression.

Figure 2:
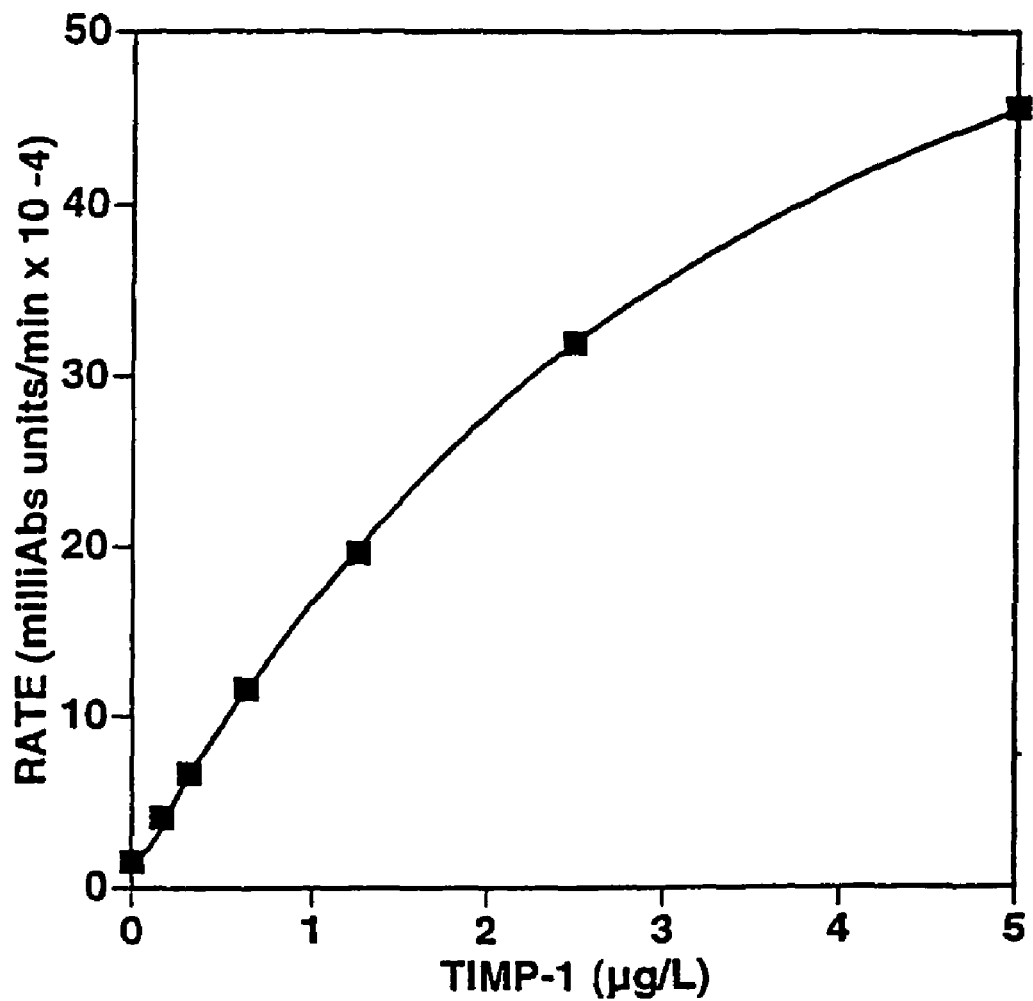

FIG. 2: TIMP-1 standard curve. Absorbance unitsfor triplicate TIMP-1 standards in the range of 0 to 5 µg/L are collected automatically over 60 minutes, with readings taken at 405 nm every 10 min. Progress curves are computed for each well and the rates obtained are fitted to a standard curve using a four-parameter equation of the form $y=d+[(a-d)/(1+(x/c)^b)]$. In the example shown, the four derived parameters had the following values: a=1.87, b=1.11, c=3.35, d=73.5. The correlation coefficient for the fitted curve is >0.999.

Figure 3:
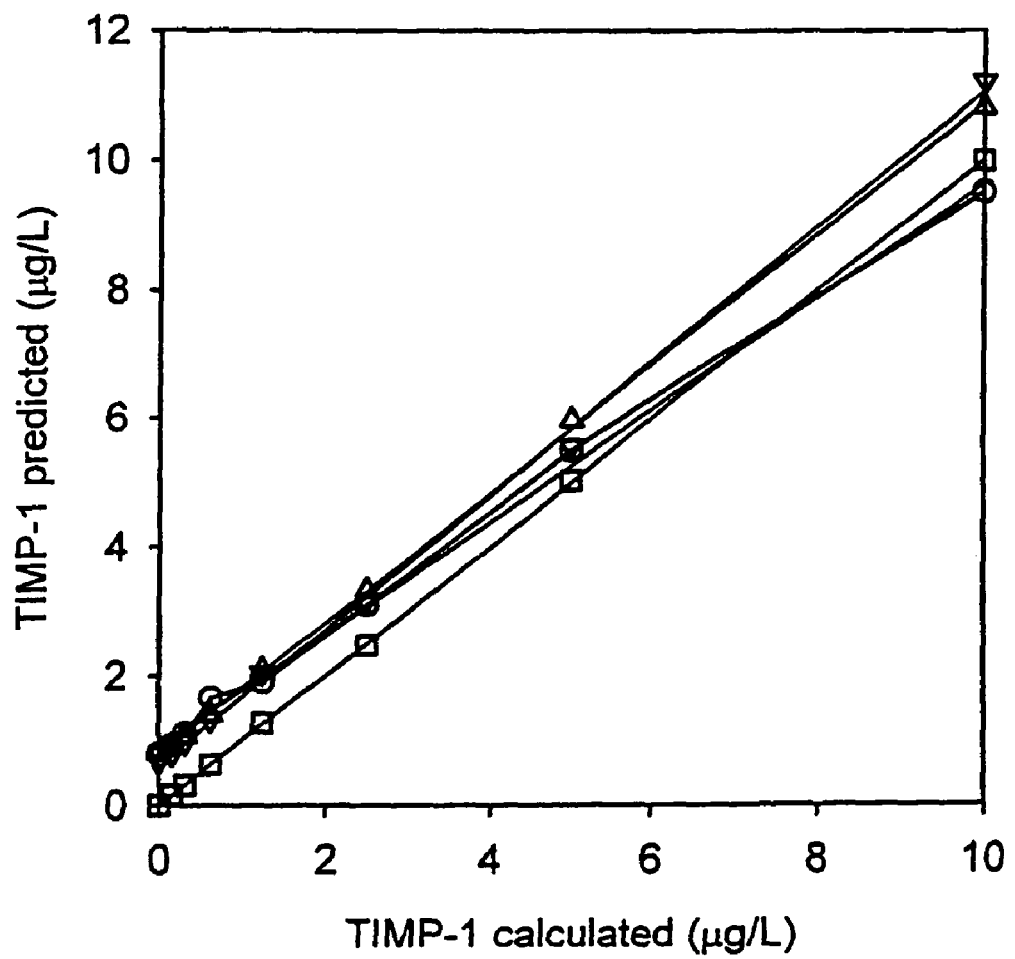

FIG. 3: Recovery of signal from standard TIMP-1 added in increasing, concentration to assay dilution buffer ($\square$-$\square$), a 1:100 dilution of EDTA plasma pool ($\Delta$-$\Delta$), a 1:100 dilution of citrate plasma pool ($\nabla$-$\nabla$) and a 1:100 dilution of heparin plasma pool (O-O). The values shown are the means of triplicates. The correlation coefficient for each fitted curve is greater than 0.99.

Figure 4:
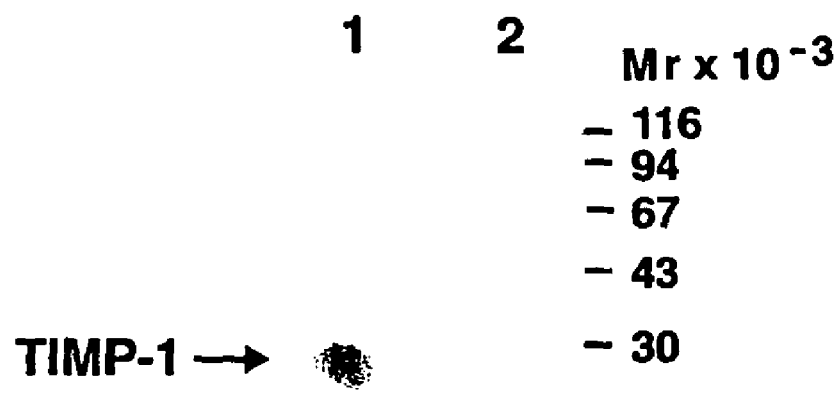

FIG. 4: Western blotting of immunoabsorbed patient plasma sample. Lane 1: standard TIMP-1; lane 2: eluate of patient citrate plasma sample diluted 1:10 and immunoabsorbed with sheep polyclonal anti-TIMP-1. Bands of non-reduced standard TIMP-1 and TIMP-1 isolated from plasma sample both appear just below 30 kDa.

Figure 5A:
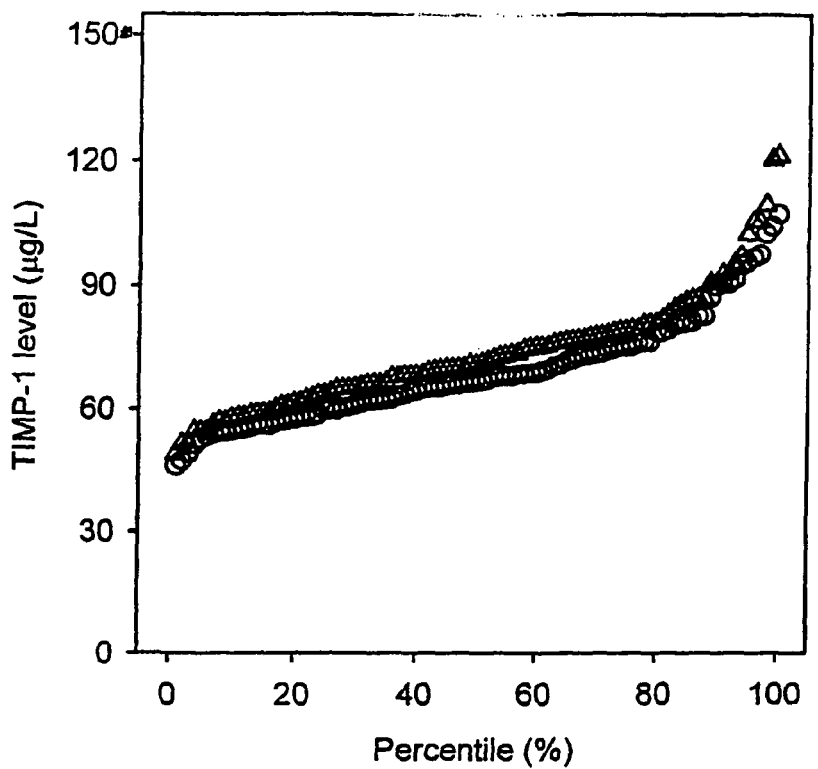

FIG. 5a: Percentiles plot for the level of TIMP-1 (µg/L) measured in citrate plasma (O) and EDTA plasma ($\Delta$) from the same individual in a set of 100 volunteer blood donors.

Figure 5B:
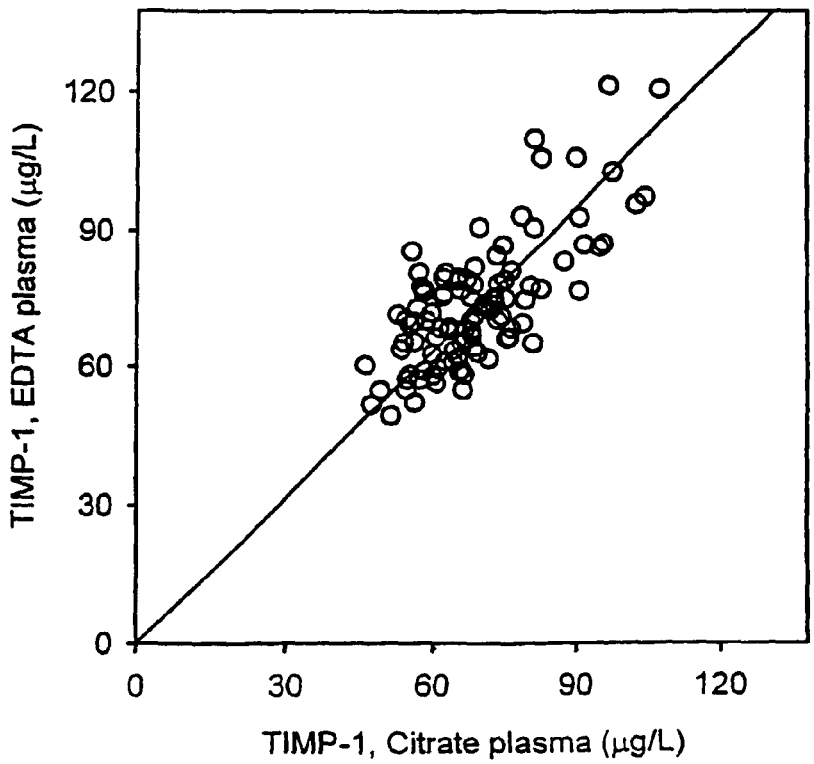

FIG. 5b: Linear regression plot for the level of TIMP-1 in citrate plasma samples compared with EDTA plasma samples from the same 100 individuals. The equation of the fitted line is y=0.93x, with a regression coefficient of 0.99.

Figure 6:
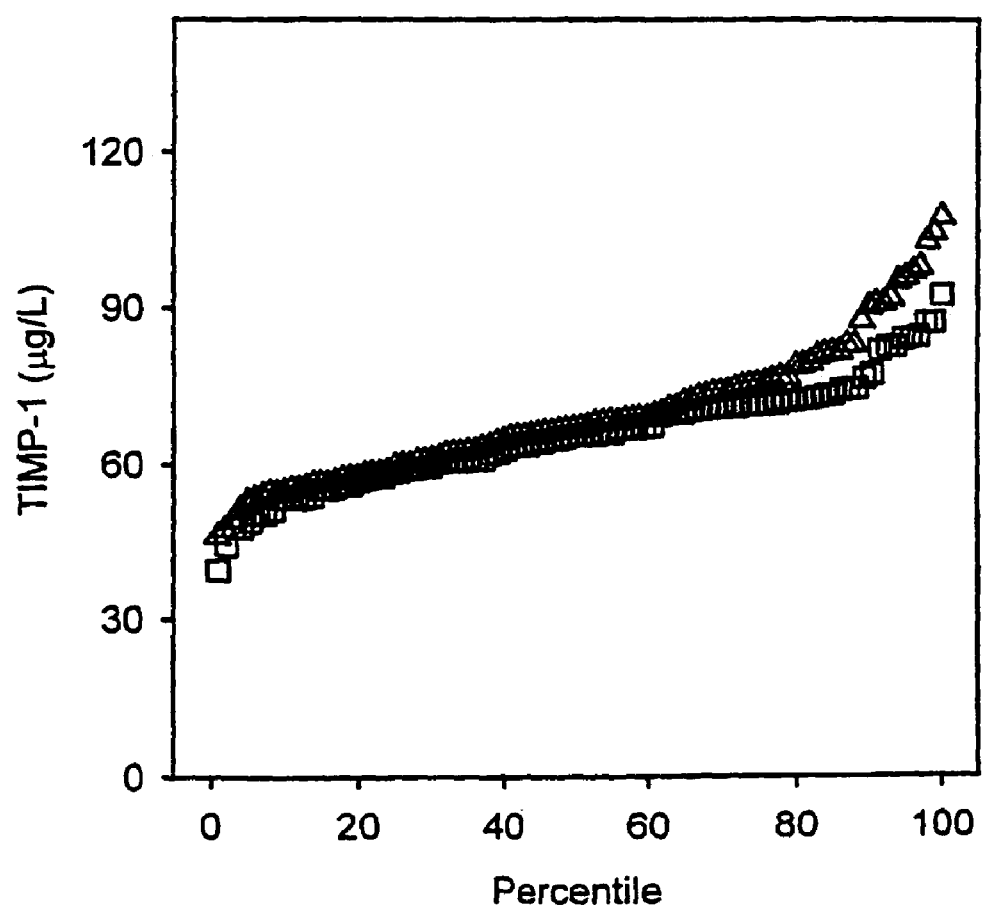

FIG. 6: Percentiles plot for the levels of TIMP-1 (µg/L) measured in two sets of citrate plasma samples obtained by the same procedure from volunteer blood donors at different times 100 samples from May=97 ($\Delta$) and 94 samples from Sept=96 ($\square$).

Figure 7:
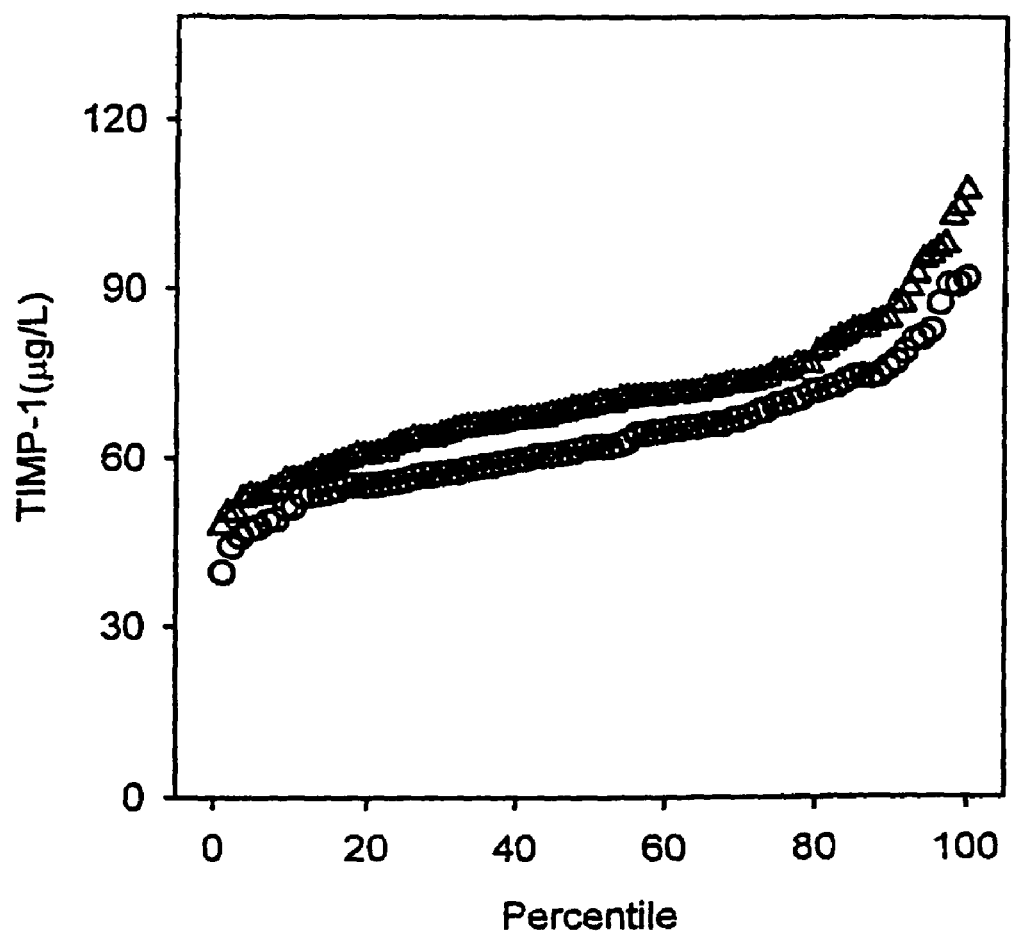

FIG. 7: Percentile plot for the levels of TIMP-1 (µg/L) measured in 194 citrate plasma samples from volunteer blood donors and stratified by sex into 107 males ($\Delta$) and 87 females (O).

Figure 8:
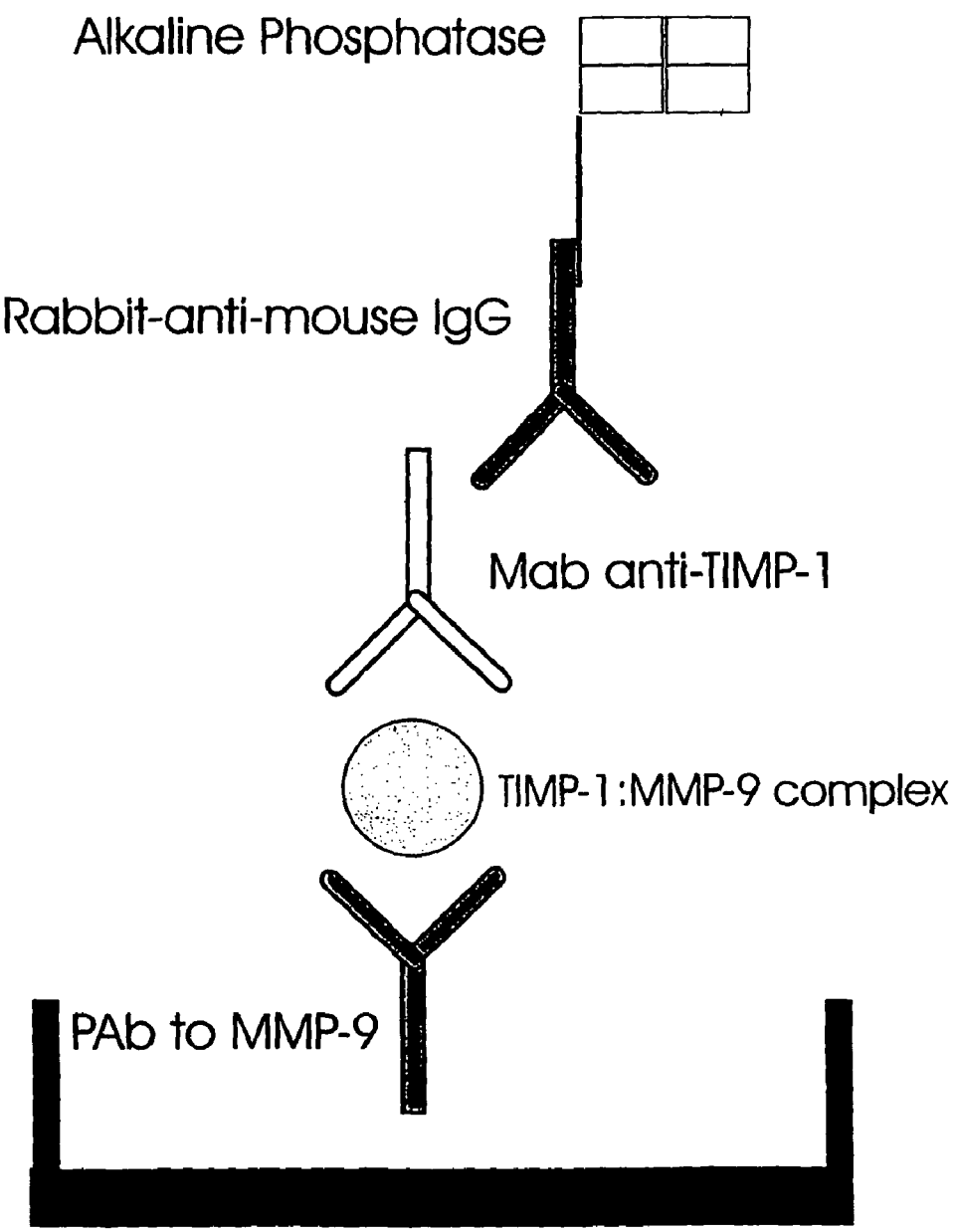

FIG. 8: Graphical illustration of the TIMP-1:MMP-9 complex ELISA.

Figure 9:
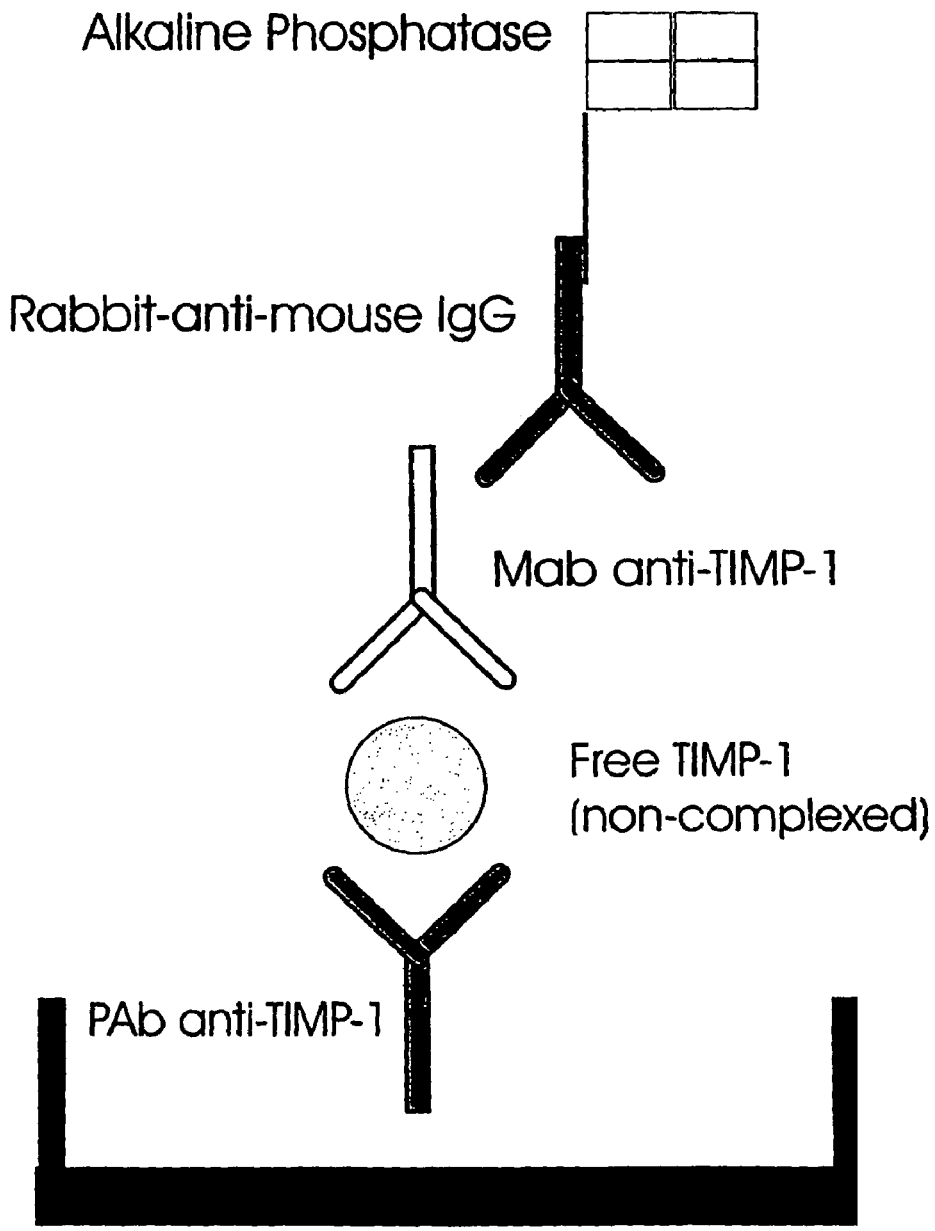

FIG. 9: Graphical illustration of the free TIMP-1 ELISA.

Figure 10:
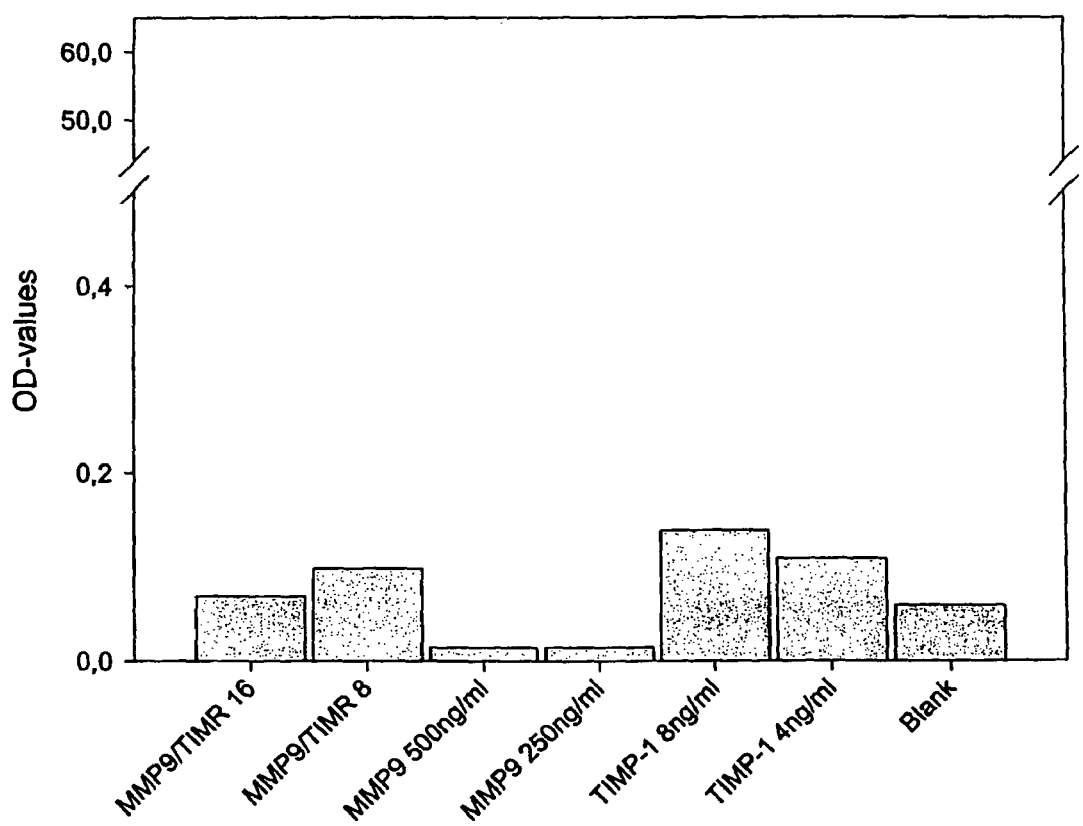

FIG. 10: A plate was coated with the polyclonal anti-MMP-9 antibody. Different concentrations of TIMP-1:MMP-9 complex, free MMP-9, free TIMP-1 and a blank control were added. Only TIMP-1:MMP-9 complexes and free MMP-9 were bound by the capture polyclonal anti-MMP-9 antibody. MAC19 was then added for antigen detection. Neither TIMP-1:MMP-9 complex nor free MMP-9 were detected by MAC19, defining the specificity of this antibody for free TIMP-1.

Figure 11:
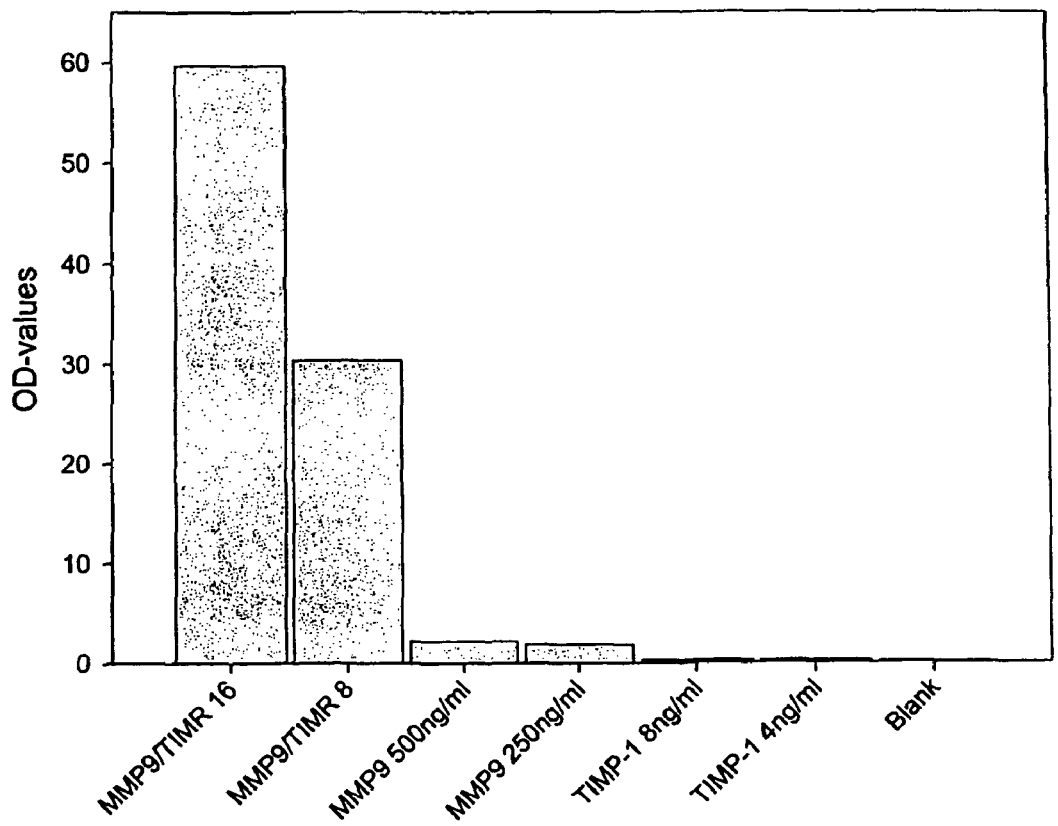

FIG. 11: A plate was coated with the polyclonal anti-MMP-9 antibody. Different concentrations of TIMP-1:MMP-9 complex, free MMP-9, free TIMP-1 and a blank control were added. Only TIMP-1:MMP-9 complexes and free MMP-9 were bound by the capture polyclonal anti-MMP-9 antibody. MAC15 was then added for antigen detection. Only TIMP-1:MMP-9 complex bound by the capture polyclonal anti-MMP-9 antibody was detected, by MAC15. Free MMP-9 was not detected by MAC15.

Figure 12:
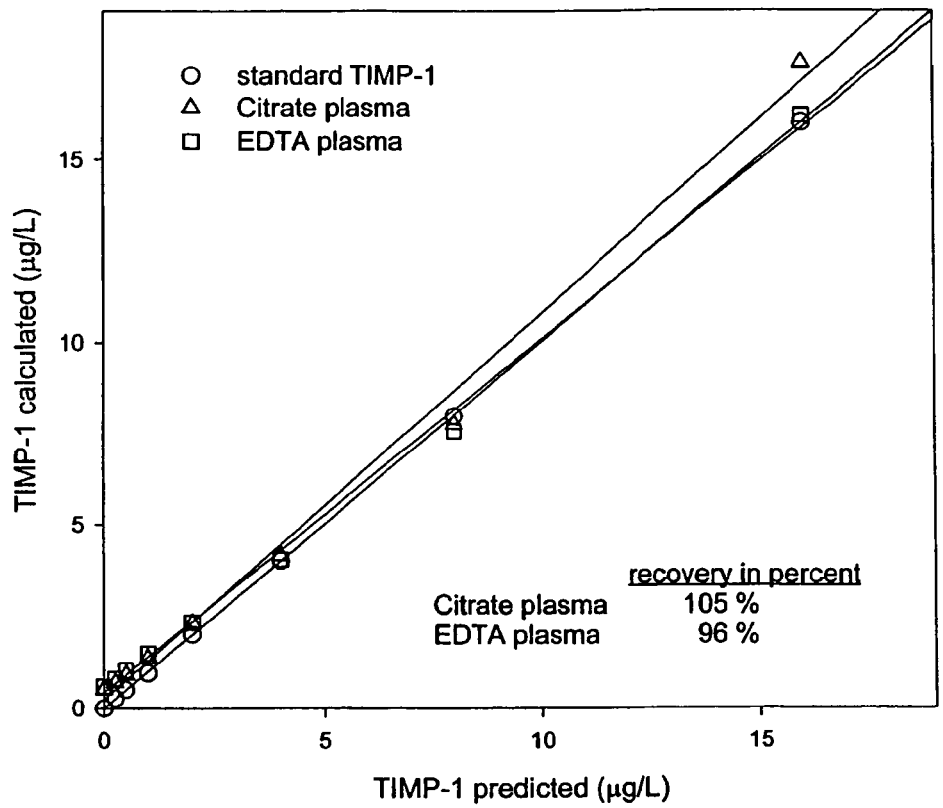

FIG. 12: Recovery of signal in the free TIMP-1 assay from standard TIMP-1 added in increasing concentration to assay dilution buffer ($\square$-$\square$), a dilution of EDTA plasma pool ($\Delta$-$\Delta$), a dilution of citrate plasma pool ($\nabla$-$\nabla$), and a dilution of heparin plasma pool (O-O). The values shown are the means of triplicates. The correlation coefficient for each fitted curve is greater than 0.99.

FIG. 13: ROC curves for total TIMP-1 in all colorectal cancer patients, in rectal cancer patients separately and in colon cancer patients separately. As healthy control subjects, a cohort of 108 healthy blood donors was used. (Number in parenthesis=Area under curve)

FIG. 14: ROC curves for total TIMP-1 in all colorectal cancer patients with Dukes' A or B disease. In addition, ROC curves for Dukes' A or B patients with colon cancer or with right sided colon cancer is included. (Number in parenthesis=Area under curve)

FIG. 15: ROC curve for total TIMP-1 from an independent set of 64 colorectal cancer patients compared to 108 healthy blood donors is shown. (AUC=Area under curve)

Figure 16:
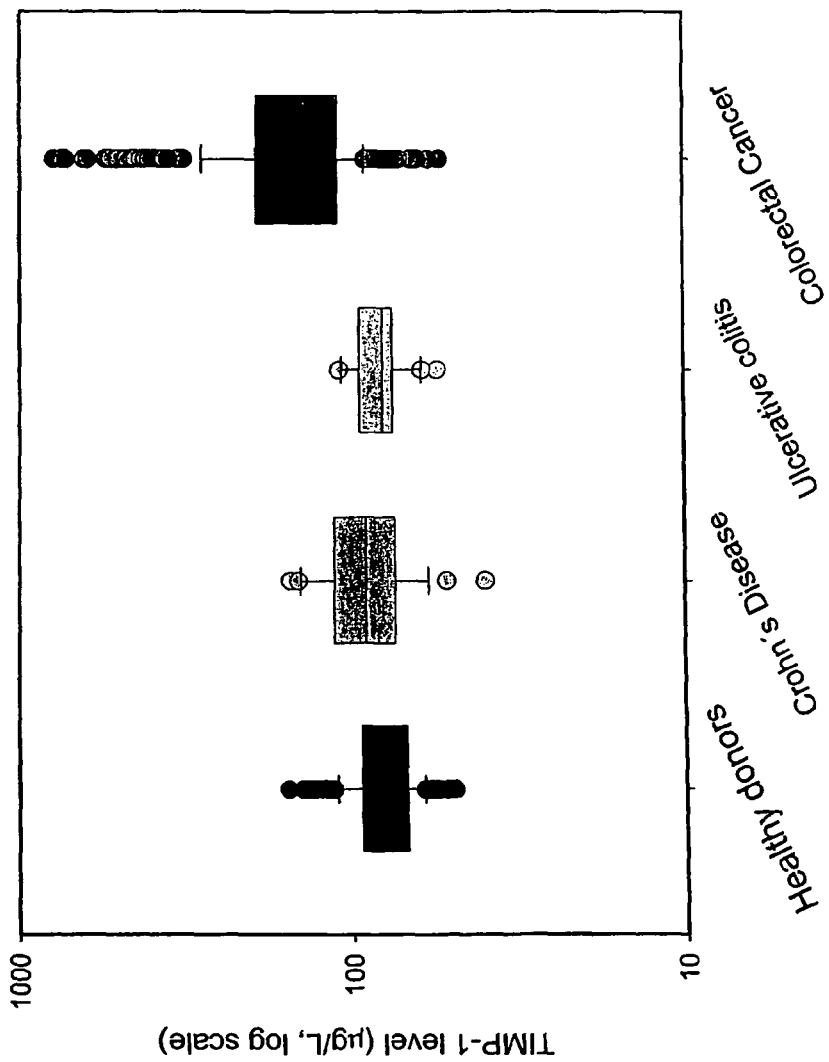

FIG. 16: Box plot showing total TIMP-1 concentrations in plasma from healthy blood donors, from patients with Crohn's Disease, from patients with ulcerative colitis and from patients with colorectal cancer. Medians, 10th, 25th, 75th and 90th centiles are shown.

Figure 17:
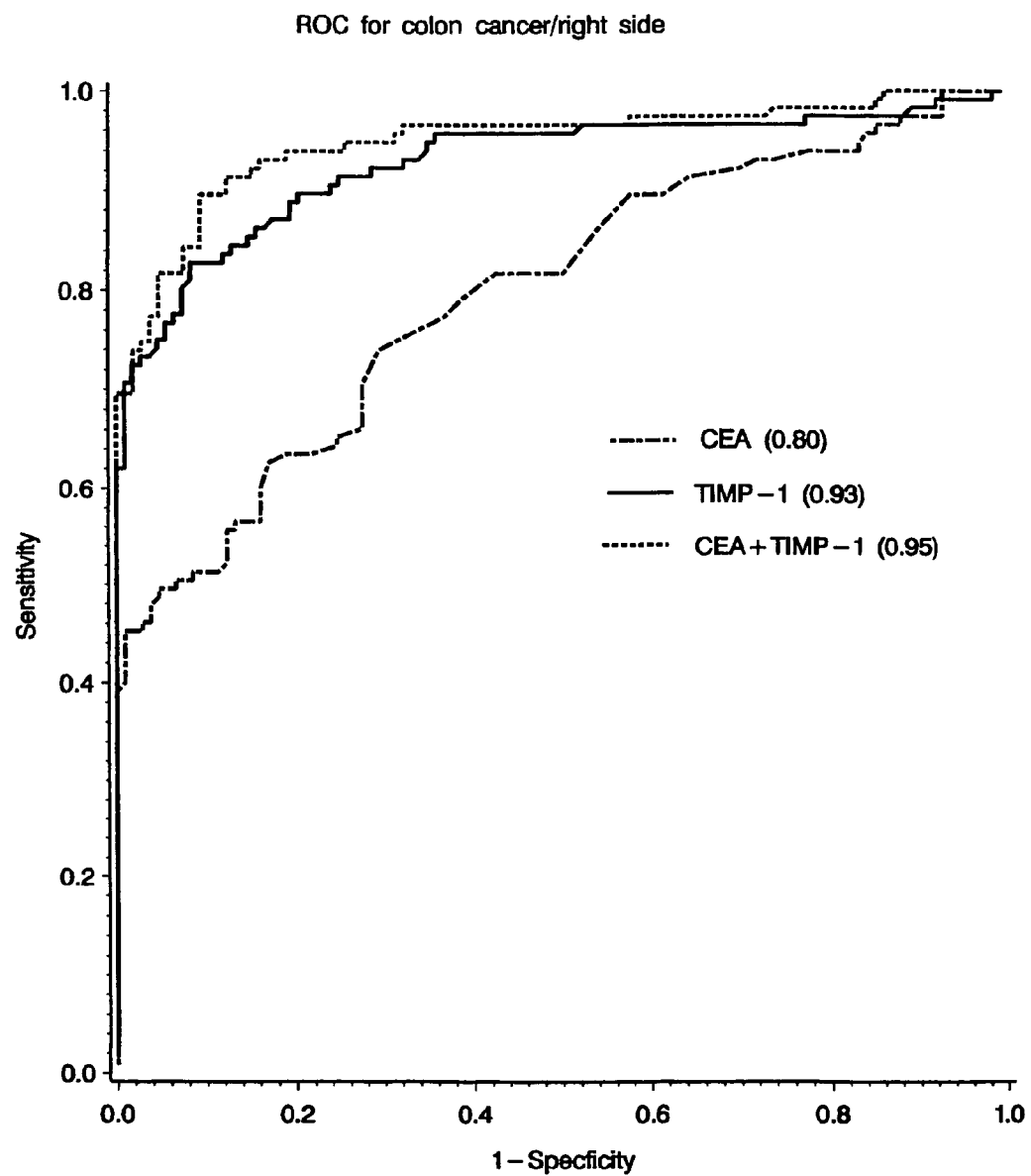

FIG. 17: ROC curves for total TIMP-1, CEA, and for the combination of total TIMP-1 and CEA in patients with right colon cancer patients and 108 healthy blood donors. (Number in parenthesis=Area under curve)

Figure 18:
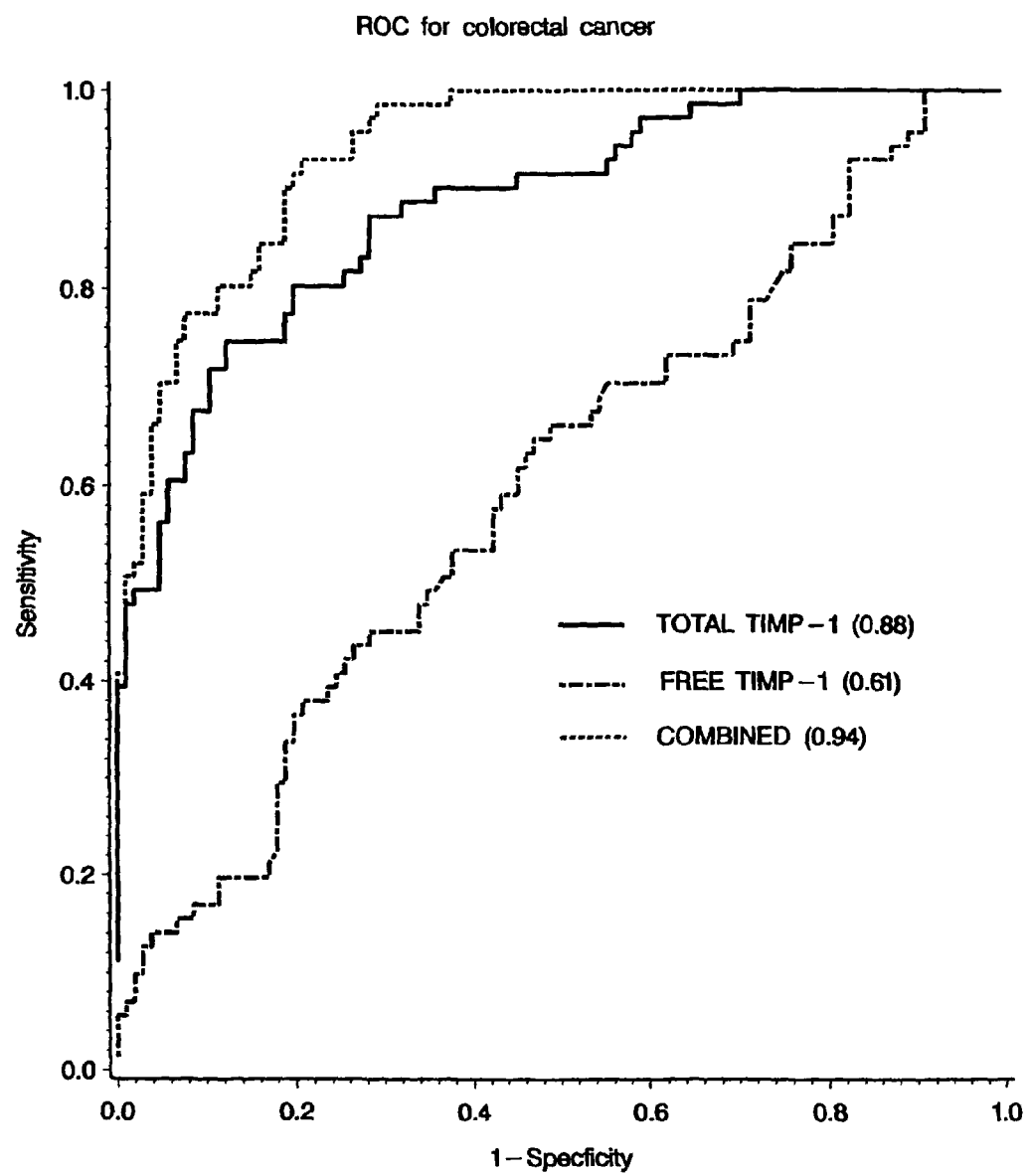

FIG. 18: ROC curves for plasma free TIMP-1, for plasma total TIMP-1 and for the combination hereof in 64 CRC patients and 108 donors. (Number in parenthesis=Area under curve)

Figure 19:
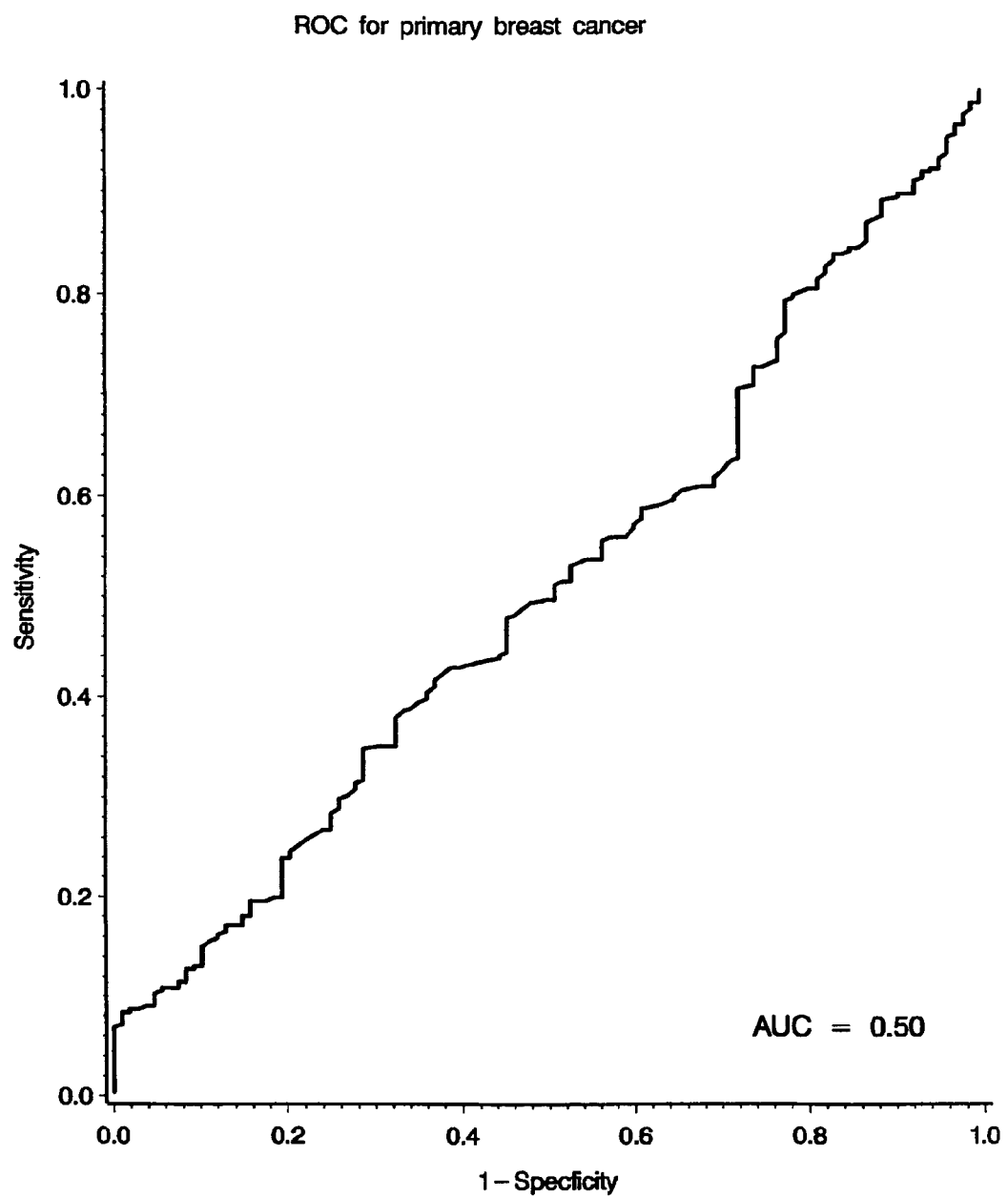

FIG. 19: ROC curve for 322 primary breast cancer patients and 108 blood donors. (AUC=Area under curve)

Figure 20:
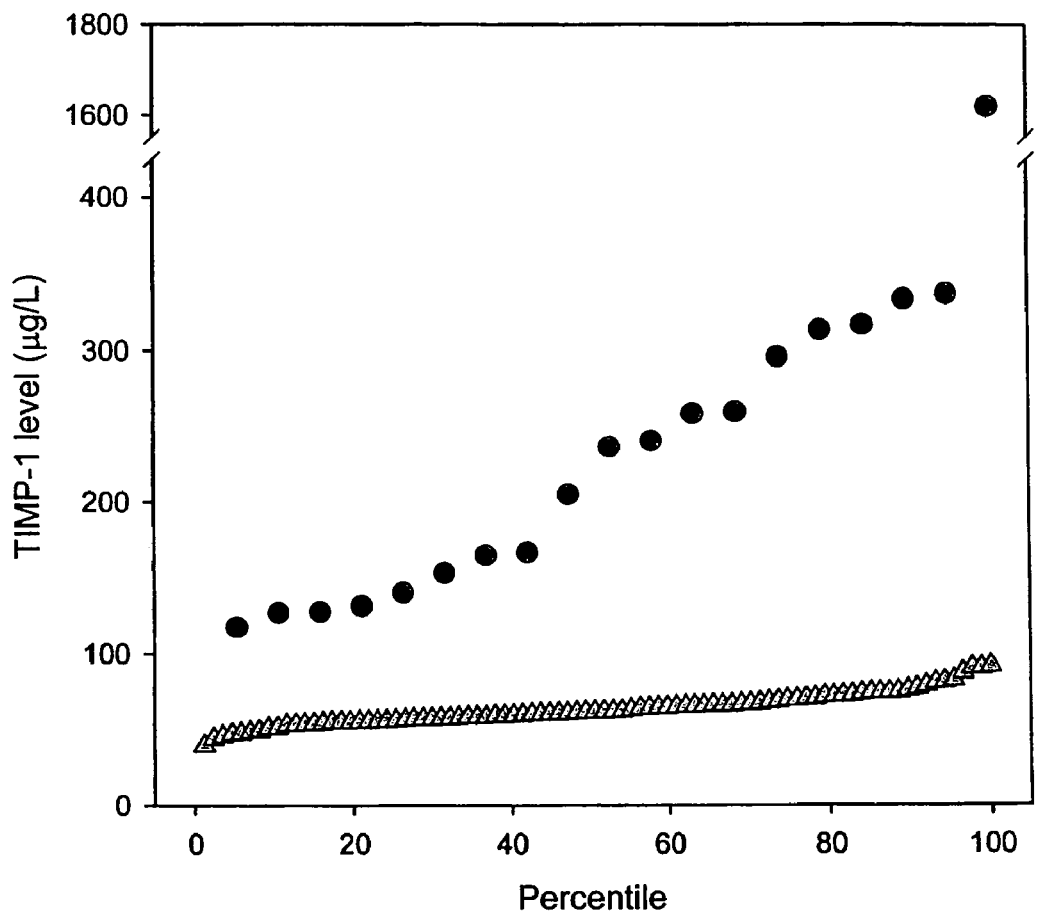

FIG. 20: Percentiles plot for the level of total TIMP-1 (µg/L) measured by ELISA in 19 EDTA plasma samples from female breast cancer patients (O) and 87 healthy blood donors (Δ).

EXAMPLES

Example 1

Preparation of an ELISA to quantitate total TIMP-1 concentrations in human plasma.

This example describes the preparation and validation of an ELISA that measures total TIMP-1 levels in plasma. In addition, this example provides information on TIMP-1 levels in different plasma preparations as well as in healthy blood donors of both sexes.

Materials and Methods:

Blood Donors

Blood samples were initially obtained from 94 apparently healthy volunteer blood donors, comprising 51 males aged 19 to 59 years (median: 41 years) and 43 females aged 20 to 64 years (median: 36 years). In a subsequent collection, 100 donor samples were obtained, comprising 56 males aged 19 to 59 years (median 42: years) and 44 females aged 20 to 60 years (median: 36.5 years). Informed consent was obtained from all donors, and permission was obtained from the local Ethical Committees.

Blood Collections and Plasma Separation

Peripheral blood was drawn with minimal stasis (if necessary a maximum of 2 min stasis with a tourniquet at maximum+2 kPa was acceptable) into pre-chilled citrate, EDTA, or heparin collection tubes (Becton-Dickinson, Mountain View, Calif.), mixed 5 times by inversion, and immediately chilled on ice. As soon as possible (no later than 1.5 h after collection) the plasma and blood cells were separated by centrifugation at 4° C. at 1,200×g for 30 min, and stored frozen at −80° C. prior to assay. Plasma pools were made with freshly collected samples from at least ten donors, aliquoted and stored frozen at −80° C. For analysis, the samples were quickly thawed in a 37° C. water bath at and then placed on ice until needed.

Total TIMP-1 ELISA

A sensitive and specific sandwich ELISA was prepared, using TIMP-1 antibodies developed at the Strangeways Laboratories (Hembry et al, 1985). A sheep polyclonal anti-TIMP-1 antiserum (Hembry et al, 1985; Murphy et al, 1991) was used for antigen capture, and a murine monoclonal anti-TIMP-1 IgG1 (MAC-15) (Cooksley et al, 1990) for antigen detection. A rabbit anti-mouse immunoglobulin/alkaline phosphatase conjugate (Catalog number D0314, Dako, Glostrup, Denmark) was the secondary detection reagent. The latter conjugate was supplied preabsorbed against human IgG, thus eliminating cross-reactivity with IgG in the plasma samples. As the monoclonal detection antibody MAC-15 recognises both free TIMP-1 and TIMP-1 in complex with MMP's (Cooksley et al, 1990), the total TIMP-1 content captured by the sheep polyclonal anti-TIMP-1 antiserum was quantitated by the ELISA.

96-well microtiter plates (Maxisorp, Nunc, Roskilde, Denmark) were coated for 1 h at 37° C. with 100 µL/well of polyclonal sheep anti-TIMP-1 (4 mg/L) in 0.1 mol/L carbonate buffer, pH 9.5. The wells were then rinsed twice with 200 µL/well of SuperBlockJ solution (Pierce Chemicals, Rockford, Ill.) diluted 1:1 with phosphate-buffered saline (PBS). The microtiter plates were stored for up to 14 days at −20° C. On the day of analysis, the plates were thawed at room temperature and washed 5 times in PBS containing 1 g/L Tween.

A series of purified, recombinant human TIMP-1 standards were used to calibrate each plate. Standards were prepared by serially diluting a stock solution of purified TIMP-1. Standard concentrations were 10, 5, 2.5, 1.25, 0.625, 0.313 and 0.156 µg/L. Included on each plate was a blank containing only sample dilution buffer, and 2 controls made from a 1:100 dilution of a citrate plasma pool. One control was added as the first sample on the plate and the second control was added as the last. All plasma samples were diluted 1:100 in sample buffer consisting of 50 mol/L phosphate, pH 7.2, 0.1 mol/L NaCl, 10 g/L bovine serum albumin (Fraction V, Boehringer-Mannheim, Penzberg, Germany), and 1 g/L Tween-20. A total of 100 µL/well of each standard, blank, control, and patient sample was incubated on the plate for 1 h at 30° C. All standards, blanks, controls, and samples were run in triplicate on each plate for every assay. After primary incubation, the wells were washed 5 times, then treated for 1 h at 30° C. with 100 µL/well of purified MAC-15 monoclonal antibody (0.5 mg/L) in sample dilution buffer. After another 5 washes the wells were incubated for 1 h at 30° C. with 100 µL/well of rabbit anti-mouse immunoglobulins (Ig)/alkaline phosphatase conjugate diluted 1:2000 in sample dilution buffer. Following 5 washes with washing solution and 3 washes with distilled, water, 100 µL of freshly made p-nitrophenyl phosphate (Sigma, St. Louis, Mo.) substrate solution (1.7 g/L in 0.1 mol/L Tris.HCl, pH 9.5, 0.1 mol/L NaCl, 5 mmol/L $MgCl_2$) was added to each well. The plate was placed in a Ceres 900J plate reader (Bio-Tek Instruments, Winooski, Vt.) at 23° C. with the yellow color development automatically monitored. Readings were taken at 405 nm against an air blank every 10 min. for one hour. KinetiCalc II software was used to analyze the data by calculating the rate of color formation for each well (linear regression analysis), generating a 4-parameter fitted standard curve, and calculating the TIMP-1 concentration of each plasma sample.

Recovery Experiments

The recovery of TIMP-1 signal was measured following addition to 1:100 dilutions of citrate, EDTA or heparin plasma pools. Purified TIMP-1 was added to plasma pools to give final concentrations in the range of 0 to 10 µg/L. The recovery in each case was calculated from the slope of the line representing TIMP-1 signal as a function of concentration, where 100% recovery was defined as the slope obtained when TIMP-1 was diluted in sample dilution buffer.

Immunoblotting

Citrate plasma from a patient with a high level of TIMP-1 in blood (634 µg/L, determined by ELISA), was diluted 1:10 and added to a protein A-Sepharose column pre-incubated with polyclonal sheep anti-TIMP-1. Following 5 cycles, bound proteins were eluted from the column and 50 µL of the resulting eluate run on 12% SDS-gel electrophoresis (Ready GelJ, Bio-Rad). A mixture of low molecular weight (Pharmacia) and high molecular weight markers (Bio-Rad) and 50 µL of TIMP-1 standard (100 µg/L) in Laemmli Sample Buffer were also run on the gel. Proteins were transferred electrophoretically from the gel onto a polyvinylidene difluoride (PVDF) membrane (Millipore). The membrane was incubated for 1 h at room temperature with 1% skim milk powder in TBS. Following washing, the membrane was incubated for 1 h at room temperature with 20 ml of MAC-15 (5 mg/L). The membrane was then washed and incubated for an additional hour at room temperature with 20 ml of rabbit anti-mouse Ig/alkaline phosphatase conjugate diluted 1:1000. Finally the membrane was washed and color developed by the addition of a phosphate substrate solution (NBT/BCIP).

Results:

ELISA Performance

Development of color in each well progressed as a linear function of time for all concentrations of total TIMP-1 in the se experiments (FIG. 1), with correlation coefficients for the fitted lines typically greater than 0.99. The standard curve for the rates plotted against the TIMP-1 concentration consisted of the linear and upper curved regions (over the range of 0 to 5μg/L) of a sigmoidal curve, and the correlation coefficient for the 4-parameter fit was typically better than 0.999 (FIG. 2). The rate with no TIMP-1 (read against an air blank) was 1.21±0.15 (mean±SD) milliabsorbance units/min (n=29), while the rate with 10 μg/L standard TIMP-1 was 50.3±6.01 milliabsorbance units/min (n=29). The limit of detection for the assay, defined as the concentration of TIMP-1 corresponding to a signal 3 SD above the mean for the TIMP-1 blank, was 0.089 μg/L. This value was 13% of the mean of the measured concentrations of TIMP-1 in healthy citrate plasma samples. The intra-assay coefficient of variation (CV) for 16 replicates of a control citrate plasma pool was 5.3%, and the inter-assay CV for 29 successive assays of the plasma pool (run on different days) was 6.2%. This plasma pool had a TIMP-1 concentration of 57.8 μg/L, corresponding to the 22nd centile of the normal individuals.

Recovery of recombinant TIMP-1 after dilution in plasma Specific recovery was determined by addition of increasing concentrations of purified TIMP-1 to a panel of plasma pool replicates, followed by subsequent measurement of signal. Recovery was 104% in citrate plasma, 101% in diluted EDTA plasma, and 87% in diluted heparin plasma (FIG. 3). Thus the recovery of TIMP-1 signal from an internal standard was acceptable for all preparations of plasma.

Dilution Curves for Total Plasma TIMP-1 Signal

Serial dilutions of citrate, EDTA and heparin plasma pools were made to test for linear reduction in TIMP-1 signal. Citrate, EDTA and heparin plasmas all gave good linearity of signal as a function of dilution. The 1% plasma dilution which was chosen for subsequent determinations lay well within the range of this linear dilution curve.

Immunoblotting of Total Plasma TIMP-1

A Western blot of an immunoabsorbed patient plasma sample showed a clear band of 28 kDa (FIG. 4, lane 2), corresponding to free, uncomplexed TIMP-1 (FIG. 4, lane 1). No bands were found at the expected higher molecular weights corresponding to complexes between MMP's and TIMP-1, e.g. MMP-2:TIMP-1, 100 kDa. This indicates either that the major part of TIMP-1 was present in the plasma as the free form, or that complexes were dissociated during SDS-PAGE. Although the sample was left both unreduced and unheated in order to preserve any complexes present in the plasma sample, it has been reported that MMP:TIMP complexes may be unstable in SDS-PAGE (Wilhelm et al, 1989; Stetler-Stevenson et al, 1989; Moll et al, 1990), even under non-reducing conditions (Moutsiakis et al, 1992).

Total TIMP-1 in Citrate and EDTA Plasma from the Same Healthy Donor

A collection of citrate and EDTA plasma samples taken simultaneously from 100 healthy donors was available for this study. These samples were not specifically collected as platelet-poor plasma. However, a small, representative number of samples, prepared as platelet-poor plasma, did not differ significantly in total TIMP-1 values. The percentile plots for total TIMP-1 levels in these samples are shown in FIG. 5a. The values in each set approximated a normal distribution. Citrate plasma TIMP-1 levels ranged between 55.0 and 90.3 μg/L (10th to 90th percentile) with a mean of 69.2±13.1 μg/L. Similarly, EDTA plasma TIMP-1 levels ranged from 58.0 to 91.8 μg/L with a mean of 73.5±14.2 μg/L. For both citrate and EDTA plasma, the mean TIMP-1 levels were in close proximity to the median levels (Table 1). A paired means comparison showed that the level of TIMP-1 in citrate plasma was significantly lower by 4.34 μg/L (95% Cl 2.34-6.33; (p<0.0001) than the EDTA plasma level from the same individual. However, it is likely that this difference may be due to the variability in sampling procedure during plasma collection. EDTA plasma tubes contained dry anticoagulant material, while citrate plasma tubes contained a small amount of liquid citrate buffer which gave a small and variable systematic dilution error (x 9/10). The level of TIMP-1 in citrate plasma correlated with that in EDTA plasma from the same individuals. The linear regression plot in FIG. 5b shows a regression coefficient of 0.99 with a slope of the fitted line of 0.93, perhaps illustrating this small dilution error. A non-parametric Spearman's rank test for the data set gave a rho value of 0.62 and p<0.0001

Total TIMP-1 Levels in Citrate Plasma

A total of 194 citrate plasma samples from healthy blood donors were assayed, comprising 94 samples taken during one collection and 100 samples taken 9 months later from a different set of donors. FIG. 6 shows the percentile plots for TIMP-1 levels measured in these two independent groups. The reference range for TIMP-1 levels in citrate plasma from the first collection was 53.3 to 77.7 μg/L (10th to 90th percentile) with a mean of 65.4±10.1 μg/L which was indistinguishable from the median (Table 1). and approximating a normal distribution. The mean TIMP-1 level for the second collection was 69.2±13.1 μg/L (reference range 55.0 to 90.3 μg/L). An unpaired means comparison showed that TIMP-1 levels in the two sets of samples taken during two different periods differed only by 3.82 μg/L (95% Cl: 0.50-7.14 μg/L; p=0.024). Moreover, no significant difference was apparent between the controls (n=8) included in each set of assays (mean difference 0.36 μg/L; 95% Cl: 1.71-2.44 μg/L; p=0.69). The mean TIMP-1 level for all 194 citrate plasma samples was 67.3±11.8 μ/L, close to the median of 66.1 μg/L, with levels again approximating a normal distribution. (reference range 54.0 to 82.7 μg/L).

TABLE 1

SUMMARY OF TOTAL TIMP-1 LEVELS DETERMINED IN BLOOD FROM HEALTHY DONORS:

| Blood fraction | Date of sampling | Number of samples | Mean ± SD (μg/L) | Median (μg/L) | Reference range* (μg/L) |
|---|---|---|---|---|---|
| Citrate plasma | September 96 | 94 | 65.4 ± 10.1 | 65.6 | 53.3-77.7 |
| Citrate plasma | May 97 | 100** | 69.2 ± 13.1 | 67.0 | 55.0-90.3 |
| Citrate plasma | 96 + 97 | 194 | 67.3 ± 11.8 | 66.1 | 54.0-82.7 |
| EDTA plasma | May 97 | 100** | 73.5 ± 14.2 | 71.2 | 58.0-91.8 |

*The reference range is defined as the 10th to 90th percentile.
**These samples were collected from the same donors.

Tests for Correlations to Gender and Age of the Donor

In these studies, the control values measured in each assay had a CV of 2.7%. Percentiles for TIMP-1 levels in 194 citrate plasma samples calculated according to gender are shown in FIG. 7. The mean TIMP-1 value for 107 male donors was 70.4±12.0 μg/L (median 69.4 μg/L) with a reference range from 56.2 to 86.6 μg/L, while the mean TIMP-1 value for 87 female donors in this set was 63.5±10.5 μg/L (median: 62.0 μg/L) with a reference range from 51.8 to 77.0 μg/L. There was a significant difference (p<0.0001) in TIMP-1 mean levels between the two groups, with males having higher TIMP-1 levels than females. There was a trend towards an increase in plasma TIMP-1 with increasing age (Spearman's rho=0.33, P=0.0011), but this did not increase with gender (females: Spearman's rho=0.29, P=0.006; males: Spearman's rho=0.35, P=0.0003). In EDTA plasma, the mean TIMP-1 value for 56 males was 76.9±15.0 μg/L (median: 75.1 μg/L) with a range from 58.8 to 96.9 μg/L, while 44 female donors had a mean TIMP-1 level of 69.3±11.8 μg/L (median: 67.9) with a reference range from 56.1 to 85.5 μg/L. Again, a significant difference appeared between males and females (p=0.0076, unpaired means comparison).

Discussion:

The assay described above enables accurate determination of total TIMP-1 in human plasma samples. Kinetic rate assays of the bound antigen were easily accomplished, permitting automated fitting of rate curves, which has proven considerably more reliable than single end-point measurements. The use of a rapid blocking agent and a dilution buffer with high buffering capacity also contributed to reproducible assays. Incorporating all these elements in the final assay fulfilled the requirements of sensitivity, specificity, stability, and good recovery of an internal standard.

The quantitative studies in blood from healthy donors showed that both citrate and EDTA plasma samples are suitable for TIMP-1 determination. Compared to other published studies of TIMP-1 i from healthy donors (Jung et al, 1996; Jung et al, 1996), levels in the present study fell within a very narrow range. Some studies have reported results in serum, but plasma was selected for the present study to avoid the variable contribution of platelet activation to the measured TIMP-1 values (Cooper et al, 1985). While the plasma samples used in this study were not specifically prepared as platelet-poor plasma, it was shown, based on tests carried out in the lab, that this does not change the values. The donor material was large enough to demonstrate that TIMP-1 levels in healthy individuals (both EDTA and citrate) approximated a normal distribution, for females as well as for males. Mean TIMP-1 levels were approx. 10% higher in males than in females for both EDTA and citrate plasma. One explanation for this is a higher release rate of TIMP-1 into blood from activated platelets, reflecting a tendency towards higher incidence of thromboembolic disease in the male population. When males and females were considered separately, there was a weak correlation between TIMP-1 and age as seen for the whole population (see above).

Example 2

Preparation of an ELISA to quantitate TIMP-1:MMP-9 complexes in plasma.

The following example describes an assay to determine the concentration of TIMP-1:MMP-9 complexes in body fluids. The assay is used with plasma samples of healthy blood donors in order to establish normal ranges of this complex (Holten Andersen et al., 1999).

Materials and Methods:

TIMP-1:MMP-9 Complex ELISA

A sensitive and specific sandwich ELISA was prepared using the above-described TIMP-1 antibody, MAC-15, and a rabbit MMP-9 polyclonal antibody developed in the Hematological Department, Rigshospitalet, Denmark (Kjeldsen et al, 1992). The MMP-9 antibody was used for antigen capture and MAC-15 was used for antigen detection. A rabbit anti-mouse-Ig/alkaline phosphatase conjugate (Dako, Glostrup, Denmark) enabled a kinetic rate assay (FIG. 8). The latter conjugate was supplied preabsorbed against human IgG, thus eliminating cross-reactivity with IgG in the plasma samples. The MMP-9 antibody captured both free MMP-9 and MMP-9 complexed with TIMP-1, while MAC-15 only recognised TIMP-1. Therefore only TIMP-1:MMP-9 complexes were quantitated by this reagent pair.

To prevent spontaneous, ex vivo TIMP-1:MMP complex formation during sampling and assay procedures, a protease inhibitor (ie. Galardin, Batimastat, Marimastat) was added to the plasma sample after thawing. The addition of the protease inhibitor blocked in vitro complex formation by inhibition of the catalytic activity of the metalloproteinases.

The TIMP-1:MMP-9 assay was prepared and validated by a method similar to that described above for the total TIMP-1 assay. The TIMP-1:MMP-9 standard was prepared by incubating equimolar amounts of purified recombinant TIMP-1 and MMP-9 (activated by adding APMA) in PBS for 1 hour at 37 degrees Celsius.

Briefly, 96-well micotiter plates were coated overnight at 4° C. with 100 μL/well of rabbit polyclonal anti-MMP-9 antiserum in 0.1 mol/L carbonate buffer, pH 9.5.Prior to use, assay wells were rinsed twice with 200 μL/well of Super-Block solution diluted 1:1 with phosphate-buffered saline (PBS), and then washed 5 times in PBS containing 1 g/L Tween 20. Wells were then incubated for 1 h at 30° C. with 100 μL/well of plasma diluted in sample buffer A series of purified TIMP-1:MMP-9 standards were used to calibrate each plate. Standards were prepared by serially diluting a stock solution of purified TIMP-1:MMP-9 complex. Included on each plate was a blank containing only sample dilution buffer, and 2 controls made from a citrate plasma pool. One control plasma pool was added as the first sample on the plate and the second control was added as the last. All standards, blanks, controls, and samples were run in triplicate on each plate for every assay. After sample incubation and TIMP-1:MMP-9 complex binding, the wells were washed 5 times, followed by treatment for 1 h at 30° C. with 100 μL/well of MAC-15 in sample dilution buffer. After another 5 washes, the wells were incubated for 1 h at 30° C. with 100 μL/well of rabbit anti-mouse Ig/alkaline phosphatase conjugate diluted in sample dilution buffer. Following 5 washes with washing solution and 3 additional washes with distilled water, 100 μL of freshly made p-nitrophenyl phosphate substrate solution was added to each well. The plate was placed in a Ceres 900J plate reader at 23° C. with the yellow color development monitored automatically. Readings were taken at 405 nm against an air blank every 10 min for one hour. KinetiCalc II software was used to analyze the data by calculating the rate of color formation for each well (linear regression analysis), generating a 4-parameter fitted standard curve, and calculating the TIMP-1:MMP-9 concentration of each plasma sample.

Recovery Experiments

Specific recovery was determined by addition of TIMP-1:MMP-9 complex to a series of citrate, EDTA or heparin plasma pools. The recovery in each case was calculated from the slope of the line representing TIMP-1:MMP-9 complex signal as a function of concentration, where 100% recovery was defined as the slope obtained when TIMP-1:MMP-9 complex was diluted in the sample dilution buffer.

Results

ELISA Performance

Development of color in each well was a linear function of time for all concentrations of TIMP-1:MMP-9 complexes measured in these experiments, with correlation coefficients for the automatically fitted lines typically greater than 0.9. The correlation coefficient for the 4-parameter fit was typically greater than 0.999.

Recovery of TIMP-1:MMP-9 Complex after Dilution in Plasma

Specific recovery was determined by addition of increasing concentrations of TIMP-1:MMP-9 to a plasma pool and subsequent measurement of the specific signal.

Dilution Curves for Plasma TIMP-1:MMP-9

Serial dilutions of citrate and EDTA plasma pools were made and complex levels quantitated to determine the linearity of the assay. Citrate and EDTA plasmas all gave good linearity of signal as a function of dilution.

Example 3

Preparation of an ELISA to quantitate free TIMP-1 levels in plasma.

The following example describes an assay, that determines the concentration of free TIMP-1 levels in body fluids. The assay is applied to plasma samples of healthy blood donors in order to establish normal ranges of free TIMP-1.

Materials and Methods:

Free TIMP-1 ELISA

A sensitive and specific sandwich immunoassay was prepared, using a TIMP-1 monoclonal IgG1 antibody (MAC-19) developed at the Strangeways Laboratories, England (Cooksley et al, 1990) and a sheep polyclonal anti-TIMP-1 antibody. The sheep polyclonal anti-TIMP-1 antibody was used for antigen capture and the murine monoclonal MAC-19 was used for antigen detection. A rabbit anti-mouse-Ig/alkaline phosphatase conjugate was the secondary detection reagent (FIG. 9). The latter conjugate was supplied preabsorbed against human IgG, thus eliminating cross-reactivity with IgG in the plasma samples. The MAC-19 monoclonal antibody is completely specific for free TIMP-1, which therefore is the only form quantitated in this assay.

In order to test that MAC19 does not react with complexes between TIMP-1 and MMP-9, the rabbit polyclonal anti-MMP-9 antibody described in Example 2 was used for antigen capture and the mouse monoclonal antibody MAC19 for antigen detection. A rabbit anti-mouse-Ig/alkaline phosphatase conjugate was used as the secondary labelled reagent. Standard TIMP-1:MMP-9 complex, free MMP-9, free TIMP-1, and a blank control were assayed. FIG. 10 shows that TIMP-1:MMP-9 complexes bound by the polyclonal anti-MMP-9 antibody are not detected by MAC19. An equivalent experiment was performed, where MAC19 was substituted with MAC15. FIG. 11 shows the results of this experiment. It is seen that MAC15 detects TIMP-1:MMP-9 complex bound by the polyclonal anti-MMP-9 antibody.

To prevent ex vivo formation of TIMP-1:MMP complexes during the sampling and assay procedures, a protease inhibitor (ie. Galardin, Batimastat, Marimastat) was added to the plasma sample after thawing. The addition of the protease inhibitor prevented in vitro complex formation by inhibition of the catalytic activity of the metalloproteinases.

96-well microtiter plates were coated for 1 h at 37° C. with 100 µL/well of polyclonal sheep anti-TIMP-1 (4 mg/L) in 0.1 mol/L carbonate buffer, pH 9.5. The assay wells were then rinsed twice with 200 µL/well of SuperBlock solution diluted 1:1 with phosphate-buffered saline (PBS). The microtiter plates were stored for up to 14 days at −20° C. On the day of use, the plates were thawed at room temperature and washed 5 times in PBS containing 1 g/L Tween 20. Wells were then incubated for 1 h at 30° C. with 100 µL/well of triplicate 1:25 dilutions of plasma made in a sample buffer consisting of 50 mol/L phosphate, pH 7.2, 0.1 mol/L NaCl, 10 g/L bovine serum albumin (Fraction V, Boehringer-Mannheim, Penzberg, Germany) and 1 g/L -Tween 20. Standards were prepared by serially diluting a stock solution of purified free TIMP-1 to yield concentrations of 10, 5, 2.5, 1.25, 0.625, 0.313 and 0.156 µg/L. Included on each plate was a blank containing only sample dilution buffer, and 2 controls made from a citrate plasma pool diluted 1:25. One control plasma pool was added as the first sample on the plate and the second control was added as the last. All standards, blanks, controls, and samples were run in triplicate on each plate for every assay. After TIMP-1 binding, the wells were washed 5 times, then treated for 1 h at 30° C. with 100 µL/well of the purified murine monoclonal anti-TIMP MAC-19 (0.5 mg/L) in sample dilution buffer. After another 5 washes the wells were incubated for 1 h at 30° C. with 100 µL/well of rabbit anti-mouse immunoglobulins/alkaline phosphatase conjugate diluted 1:2000 in sample dilution buffer. Following 5 washes with washing solution and 3 washes with distilled water, 100 µL of freshly made p-nitrophenyl phosphate (Sigma, St. Louis, Mo.) substrate solution (1.7 g/L in 0.1 mol/L Tris.HCl, pH 9.5, 0.1 mol/L NaCl, 5 mmol/L $MgCl_2$) was added to each well, and the plate was placed in a Ceres 900J plate reader (Bio-Tek Instruments, Winooski, Vt.) at 23° C. The yellow color development was monitored automatically, with readings taken at 405 nm against an air blank every 10 min for one hour. KinetiCalc II software was used to analyze the data, to calculate the rate of color change for each well (linear regression analysis), and to compute a 4-parameter fitted standard curve, from which the free TIMP-1 concentration of each plasma sample was calculated.

Dilution Curves and Recovery Experiments

These experiments were performed essentially as described in Example 1, but using MAC19 instead of MAC15 for detection of free TIMP-1 (as described above).

Healthy Donors 108 donor plasma samples were obtained. Donors gave blood on a volunteer basis and were all apparently healthy. Informed consent was obtained from all blood donors, and permission was obtained from the local Ethical Committees. The blood sampling and handling were performed as described in Example 1.

Results

ELISA Performance

Development of color in each well was a linear function of time for all concentrations of free TIMP-1 measured in these experiments, with correlation coefficients for the automatically fitted lines typically better than 0.9. The correlation coefficient for the 4-parameter fit was typically better than 0.999. The intra-assay variation for 24 triplicate measurements of the control plasma pool was 9.6%.

Recovery of Recombinant TIMP-1 after Dilution in Plasma

Specific signal recovery was determined by addition of increasing concentrations of purified TIMP-1 standard to a plasma pool and subsequent measurement of the ELISA signal. In the diluted citrate plasma pool 105% recovery was obtained, while 96% recovery was obtained in the diluted EDTA plasma pool (FIG. 12).

Dilution Curves for Free Plasma TIMP-1 Signal

Serial dilutions of citrate and EDTA plasma pools were made and free TIMP-1 levels assayed to test for linear reduction in ELISA signal. Citrate and EDTA plasmas all gave good linearity of signal as a function of dilution.

Healthy Blood Donors

Free TIMP-1 was measurable in all plasma samples. The median free TIMP-1 concentration was 70.9 µg/L (range: 32.3-169.7 µg/L).

Discussion

This assay directly measures plasma free TIMP-1 levels. When comparing free TIMP-1 levels with total TIMP-1 levels (the latter measured with assay described in Example 1) in the 108 healthy blood donors, a correlation coefficien of 0.46 (Rho, Spearman Rank, p<0.0001) was obtained.

Example 4

Detection or screening value of Total TIMP-1 in patients with colorectal cancer.

Total TIMP-1 levels in plasma from 591 colorectal cancer patients (338 colon and 253 rectal) and in plasma from 108 age and gender matched healthy individuals were measured with the TIMP-1 assay described in Example 1. The TIMP-1 values were analyzed and compared using standard biostatistical parameters.

Materials and Methods:

Patients 591 patients undergoing elective surgery for pathologically confirmed colorectal cancer were included in the study. Blood samples were obtained preoperatively with informed consent from all patients in accordance with the Helsinki declaration, and permission was granted by the local ethical committee of Hvidovre Hospital, Denmark. All patients had pathologically verified adenocarcinoma of the colon or rectum. It was found that 59 (10%) patients could be classified as having Dukes' stage A disease, 219 (37%) patients Dukes' stage B, 170 (29%) patients Dukes' stage C and 143 (24%) patients Dukes' stage D. 338 tumors were colon cancers and 253 were rectal cancers. Clinical data such as age, sex and survival after surgery were collected. The median age of the patients was 69 years (range 33-90 years) with 237 females and 354 males represented in the patient cohort.

A second patient cohort was collected prospectively. This cohort consisted of 21 rectal cancer and 43 colon cancer patients. There were 11 patients with Dukes' stage A, 27 with Dukes' stage B, 14 with Dukes' stage C, and 13 with Dukes' stage D disease.

Healthy Donors

The same donor population as described in Example 3.

Blood Samples

Blood samples (5 ml) were collected preoperatively from all patients on the day of their surgery. To ensure valid TIMP-1 measurements, peripheral blood was drawn with minimal stasis and collected in EDTA anticoagulant tubes (Becton-Dickinson, Mountain View, Calif.) in accordance with a previously described protocol (Example 1).

TIMP-1 ELISA

TIMP-1 levels were measured in EDTA plasma samples using the assay described in Example 1.

Results:

Total TIMP-1 Levels in Plasma

Using a kinetic rate assay, total TIMP-1 levels were determined in all patient and healthy donor plasma samples. Every plasma sample had measurable levels of TIMP-1, with a median total TIMP-1 value for the 591 colorectal cancer patients of 141.1 µg/L (range 53.7-788.7 µg/L). When stratified into colon and rectal cancer, the median values were 158.6 µg/L (range: 53.7-788.7 µg/L) for colon and 126.3 (range: 64.1-640.1 µg/L) for rectal cancer. There was a statistically significant difference in TIMP-1 levels when the patient material was stratified according to Duke's stage, with Dukes' A being the lowest and Dukes' D the highest (Kruskal-Wallis test, P<0.0001). However, the highest TIMP-1 levels were not restricted to advanced disease, and no significant difference in total plasma TIMP-1 levels was seen among patients with Dukes A–C disease. A relatively weak correlation between plasma TIMP-1 and age was found (r=0.35; p<0.0001). There was no significant difference in TIMP-1 levels between males and females (p=0.97).

The median TIMP-1 level In plasma from healthy donors was 88.6 µg/L with a range of 51.0-156.2 µg/L. There was a highly significant statistical difference in the total plasma TIMP-1 values between the colorectal cancer patients and the healthy blood donors.

The median total TIMP-1 value for the 64 colorectal cancer patients was 138.2 µg/L (range: 80.7-790.6 µg/L). Stratifying the patients into colon and rectal cancer, the median, total TIMP-1 values were 152.2 µg/L (range: 80.7-626.2 µg/L) for colon and 133.6 (range: 84.3-790.6) for rectal cancer. There was a highly significant statistical difference in the total plasma TIMP-1 values between the colon and rectal cancer patients each compared with the healthy blood donors.

Detection or Screening Value of Total TIMP-1

Using the measured total TIMP-1 levels in plasma from healthy donors and the 591 colorectal cancer patients, Receiver Operating Characteristics (ROC) curves were generated to evaluate the detection or screening value of total TIMP-1. As seen in FIG. 13, the ROC curve was initially steep, indicating a high sensitivity and specificity of total TIMP-1 as a marker for colorectal cancer. It appears that the AUC is greater for colon cancer than for rectal cancer. FIG. 14 shows a similar ROC curve now including only patients with early stage colorectal cancer, i.e. Dukes' stage A or B disease. Also shown is the ROC curve for early stage (Dukes' stage A and B) right-sided colon cancer.

Using the total TIMP-1 levels in plasma from healthy donors and in the second cohort of 64 colorectal cancer patients, ROC curves were again constructed to confirm the detection or screening value of TIMP-1. As seen in FIG. 15, the curve was again initially steep, indicating a high sensitivity and specificity of total TIMP-1 as a marker for colorectal cancer.

An additional study of 180 healthy blood donors and 20 colorectal cancer patients, using different antibodies (Anti TIMP-1 11E/C6, Anti-TIMP-1 RRU-T6) (the hybridomas producing these two antibodies were deposited Apr. 10, 2000 with ATCC) in an automated immunoassay further corroborated the previous clinical results. Moreover, the absolute values generated from the automated assay showed a high degree of correlation to those obtained by the assay described in Example 1 (r=0.9).

Discussion:

These data suggest that total TIMP-1 measurements in plasma can be used as a detection or screening procedure to aid in identifying patients with a high risk of having colorectal cancer. In particular, total TIMP-1 was as effective in identifying patients with early cancer (Duke's stage A+B) as identifying patients with more advanced disease. Also, total TIMP-1 was even more effective in identifying patients with early stage, right-sided colon cancer, a procedure that is difficult with conventional detection or screening procedures. Right-sided colon cancer cannot be visualized by flexible sigmoidoscopy, a standard colon cancer screening methodology. It has a more insidious onset than do left-sided lesions, and clinical symptoms develop only in late stage disease. Early detection or screening of right sided colon cancer has the potential to reduce the mortality of this disease.

Moreover, the smaller, prospective trial corroborated the results of the larger retrospective study, further confirming the detection or screening value of total TIMP-1 in patients suffering from colorectal cancer.

Example 5

Quantitation of total TIMP-1 in plasma from patients with inflammatory bowel diseases.

Patients 46 patients with IBD (Inflammatory Bowel Disease) were included in the study. 22 patients had ulcerative colitis and 24 patients had Crohn's Disease. Total TIMP-1 levels in EDTA plasma from healthy blood donors and colorectal cancer patients (Examples 3 and 4) were included for comparison.

Total TIMP-1 Values

Total TIMP-1 levels were measured in the EDTA plasma samples using the sandwich assay described in Example 1.

Results:

The measured total TIMP-1 values are shown in Table 2.

TABLE 2

|  | Ulcerative colitis n = 22 | Crohn's disease n = 24 | IBD total n = 46 |
|---|---|---|---|
| Median total TIMP-1 (µg/L) | 79.5 | 78.3 | 84.8 |
| Range total TIMP-1 (µg/L) | 54.9-189.9 | 49.0-156.2 | 38.7-154.5 |

|  | Healthy donors n = 108 | Colorectal Cancer n = 591 |
|---|---|---|
| Median total TIMP-1 (µg/L) | 89.1 | 141 |
| Range total TIMP-1 (µg/L) | 51.0-156.2 | 53.7-789 |

There was no significant difference when total TIMP-1 values from patients with IBD and healthy blood donors were compared (Mann-Whitney; p=0.45). There was a highly significant difference between total plasma TIMP-1 levels between patients with IBD and the 591 colorectal cancer patients (Mann-Whitney; p<0.0001). A graphical representation of these results is depicted in FIG. 16.

Discussion:

These results demonstrate that patients with colorectal cancer have significantly higher total TIMP-1 plasma levels than do patients with IBD. Moreover, patients with IBD had total TIMP-1 levels equivalent to those found in healthy blood donors, showing that plasma total TIMP-1 can be used as a highly sensitive and specific marker to distinguish between non-malignant and malignant diseases of the gastrointestinal tract.

Example 6

Detection or screening value of total TIMP-1 in combination with CEA in patients with colorectal cancer.

Total TIMP-1 in plasma from 591 colorectal cancer patients (338 colon and 253 rectal) and in plasma from 108 age and gender matched healthy individuals was measured using the TIMP-1 assay described in Example 1. In addition, CEA was measured in the corresponding patient and donor serum samples using a commercially available, chemiluminescent CEA EIA kit (Immulite CEA, DPC©, Los Angeles, Calif., USA). The TIMP-1 and CEA values from healthy donors and cancer patients were combined by logistic regression analysis and ROC curves were generated.

Results:

Detection or screening value of total TIMP-1 and CEA

Calculating the sensitivity and specificity of CEA in the 591 colorectal cancer patients when including the 108 healthy donors a cut-off providing 98% specificity gave a sensitivity of 35%. When stratifying patients into colon or rectal cancer, the sensitivity was 37% and 33%, respectively at the same level of specificity. Including only patients with right-sided colon cancer, it is demonstrated in FIG. 17 that the sensitivity increased to 45%.

When the total TIMP-1 values from Example 4 are included together with CEA, the sensitivity of the marker combination was found by logistic regression analysis to be 52%. The additional sensitivity obtained by the addition of CEA measurements in serum is highly significant (p<0.0001). When stratifying the patient cohort into colon and rectal cancer, the sensitivity was 61% and 39%, respectively at the 98% specificity level. Including only patients with right-sided colon cancer, the sensitivity was 74%. A graphical illustration of these results appears from FIG. 17.

Discussion:

These data show that by adding an additional marker, an improvement in the sensitivity of total TIMP-1 can be obtained, while maintaining a high specificity of 98%. Thus, the combination of CEA and TIMP-1 could be useful as a detection or screening procedure to identify patients with a high risk of having colorectal cancer. In particular, this combination was efficient in identifying patients with early stage cancer (Duke's stage A+B). Also, this combination was highly effective in identifying patients with early stage, right-sided colon cancer.

Example 7

Lack of detection or screening value of plasma free TIMP-1 levels in patients with colorectal cancer.

Materials and Methods

Free TIMP-1 levels in plasma from 64 colorectal cancer patients (43 colon and 21 rectal) and in plasma from 108 age matched, healthy individuals were measured using the TIMP-1 assay described in Example 3. The free TIMP-1 values were analysed and compared using standard biostatistical parameters.

Results:

Free TIMP-1 Levels in Plasma

Using the kinetic rate ELISA described in Example 3, free TIMP-1 levels were measured in all patient and healthy donor plasma samples. All samples had measurable levels of free TIMP-1, with a median free TIMP-1 value of 82.0 µg/L (range: 44.7-424.0 µg/L) for the colorectal cancer patients.

The median free TIMP-1 level in plasma from healthy donors was 70.9 µg/L, with a range of 32.3-169.7 µg/L. While no significant difference in free TIMP-1 levels was found among patients with Dukes' stage A–C disease, patients with Dukes' stage D had significantly elevated free plasma TIMP-1 levels compared to the patients with Dukes' stage A and B disease. When comparing total TIMP-1 values with free TIMP-1 values in plasma from these 64 colorectal cancer patients a correlation coefficient of 0.91 (Rho, Spearman Rank, $p<0.0001$) was found.

Lack of detection or screening value of free TIMP-1

FIG. 18 shows the ROC curves generated from the plasma measurements of free TIMP-1. The AUC is 0.61 when determining the detection or screening performance of free TIMP-1.

Discussion:

These data show that free TIMP-1 alone is not likely to be useful as a screening or detection marker to identify patients with a high risk of having colorectal cancer.

Example 8

Detection or screening value of TIMP-1:MMP-9 complex measurements in patients with colorectal cancer.

TIMP-1:MMP-9 complex levels in plasma from colorectal cancer patients and in plasma from age and gender matched healthy individuals can be measured using the TIMP-1:MMP-9 assay described in Example 2. TIMP-1:MMP-9 complex values from healthy donors and cancer patients can be compared and the detection or screening value determined.

Using the measured values of free, total, and TIMP-1:MMP-9 complex levels, the detection or screening value of ratios or fractions can be calculated. In addition other molecules e.g. serum CEA can be added to these calculations to generate mathematical algorithms to increase the overall detection or screening value.

Example 9

Detection or screening value of the combination of plasma total TIMP-1 and plasma free TIMP-1 in patients with colorectal cancer.

Total TIMP-1 levels in plasma from 64 colorectal cancer patients and in plasma from 108 age and gender matched healthy individuals were measured with the TIMP-1 assay described in Example 1. Using the assay described in Example 3, plasma free TIMP-1 levels were measured in the same individuals as described above. The total and the free TIMP-1 values were analyzed and compared using logistic regression analysis.

Materials and Methods:

Patients 64 patients undergoing elective surgery for pathologically confirmed colorectal cancer were included in the study. This cohort consisted of 21 rectal cancer and 43 colon cancer patients. There were 11 patients with Dukes' stage A, 27 with Dukes' stage B, 14 with Dukes' stage C, and 13 with Dukes' stage D disease. Blood samples were obtained preoperatively with informed consent from all patients in accordance with the Helsinki declaration, and permission was granted by the local ethical committee of Hvidovre Hospital, Denmark. All patients had pathologically verified adenocarcinoma of the colon or rectum. Clinical data such as age, sex and survival after surgery were collected.

Healthy Donors

The same donor population as described in Example 3.

Blood Samples

Blood samples (5 mL) were collected preoperatively from all patients on the day of their surgery. To ensure valid TIMP-1 measurements, peripheral blood was drawn with minimal stasis and collected in EDTA anticoagulant tubes (Becton-Dickinson, Mountain View, Calif.) in accordance with a previously described protocol (Example 1).

Total and Free TIMP-1 Plasma Measurements

TIMP-1 levels were measured in EDTA plasma samples using the assays described in Example 1 and Example 3.

Results:

TIMP-1 Levels in Plasma

The total TIMP-1 levels in these 64 patients with colorectal cancer are described in Example 4, and the free TIMP-1 levels in these patients are described in Example 7.

Using the total and the free TIMP-1 levels in plasma from healthy donors and from the 64 colorectal cancer patients, ROC curves were constructed for each of these TIMP-1 forms. The total TIMP-1 values obtained confirm the detection or screening value of total TIMP-1 measurements in patients with colorectal cancer. As seen in FIG. 15, the curve was again initially steep, indicating a high sensitivity and specificity of total TIMP-1 as a marker for colorectal cancer. The ROC curve for free TIMP-1 was discussed in Example 7.

The corresponding data for total TIMP-1 in this patient population gave an AUC of 0.88. However, an increase in detection or screening value was obtained when combining free and total TIMP-1 (AUC=0.94). This increase is highly statistically significant, $p<0.0001$ and shows the value of the important embodiment of using both free and total TIMP-1 in the same analysis.

Discussion:

These data suggest that the combination of total TIMP-1 and free TIMP-1 measurements in plasma can be used as a screening or detection procedure to aid in identifying patients with a high risk of having colorectal cancer.

In a similar manner as described in the present example, other ratios and/or combinations or mathematical permutations between free and total TIMP-1 values can be calculated and used for detection or screening purposes.

Calculations of relationships among all the various forms of TIMP-1, including total and free TIMP-1, total concentration of complexes (total TIMP-1—free TIMP-1), and/or the concentration of TIMP-1:MMP-9, might be extremely useful in the management, and especially distinguishing of patients with non-malignant diseases from patients with cancer.

Example 10

Lack of detection or screening value of total TIMP-1 measurements in patients with primary (stage I and II) breast cancer.

Materials and Methods

Using the total TIMP-1 assay described in Example 1, pre-operative plasma samples from 322 patients with primary breast cancer were analysed for total TIMP-1 content. In addition, 108 plasma samples from healthy blood donors were evaluated. The median total TIMP-1 for the breast cancer patients was 88.3 µg/L (range: 45.5-289.3 µg/L), while the median total TIMP-1 level for the healthy blood donors was 88.9 µg/L (range: 51.0-156.2 µg/L). There was no statistical significant difference in total TIMP-1 plasma levels between the two groups (Mann-Whitney, p=0.87). FIG. 19 shows a ROC-curve including the above mentioned data.

Discussion

These data demonstrate that patients with primary breast cancer have total TIMP-1 values that are not significantly different from those of healthy blood donors. Thus, these data support the specificity of TIMP-1 measurements in the detection or screening of patients with colorectal cancer.

Example 11

Detection value of plasma total TIMP-1 in patients with metastatic (stage IV) breast cancer.

This example describes total TIMP-1 determinations from patients with stage IV breast cancer.

Materials and Methods:

Patients and Blood Donors

Blood was collected from 19 stage IV breast cancer patients (aged 45 to 70 years) at the Oncology Department, Herlev University Hospital, Copenhagen, Denmark, and from 87 healthy female blood donors (Example 1).

Total TIMP-1 Plasma Levels

Total TIMP-1 levels were measured in all EDTA plasma samples using the assay described in Example 1.

Results:

Total TIMP-1 Levels in Plasma from Patients with Advanced Breast Cancer

Total TIMP-1 was measured in EDTA plasma samples from 19 breast cancer patients with stage IV disease. These levels were compared with total TIMP-1 levels in 87 healthy female donors. The mean, total TIMP-1 level measured in the 19 breast cancer patients was 292±331 µg/L (median: 236 µg/L), compared, with a mean, total TIMP-1 level of 63.5±10.5 µg/L (median: 62.0 µg/L) in 87 healthy female donors. A Wald-Wolfowitz runs test indicated a highly significant difference (p<0.0001) between patient total TIMP-1 levels and those of healthy donors. FIG. 20 shows a percentile plot of total TIMP-1 levels in from the 19 breast cancer patients and the TIMP-1 levels found in plasma from the 87 healthy female donors.

Discussion:

These data show that plasma TIMP-1 measurements can be used to monitor breast cancer patients for recurrence of disease.

Example 12

Detection or screening value of TIMP-2 measurements in patients with colorectal cancer Materials and Methods TIMP-2 levels were measured with an in-house TIMP-2 assay in plasma from 64 colorectal cancer patients (43 colon and 21 rectal) and in plasma from 108 age matched healthy individuals. The measured TIMP-2 values from healthy donors and cancer patients were compared.

Results:

TIMP-2 was measurable in all samples. No significant differences in TIMP-2 levels were found between healthy blood donors and colorectal cancer patients.

Discussion

These data support the specificity of TIMP-1 measurements in the detection or screening of patients with colorectal cancer, supporting the unique value of TIMP-1 as an aid in the early detection of colorectal cancer.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

REFERENCES

Baker T, Tickle S, Wasan H, Docherty A, Isenberg D & Waxman J (1994) Serum metalloproteinases and their inhibitors: markers for malignant potential. *Br. J. Cancer* 70, 506-512.

Birkedal-Hansen H. Moore W G, Bodden M K, Windsor L J, Birkedal-Hansen-B, DeCarlo A & Engler J A (1993) Matrix metalloproteinases: a review. *Crit. Rev. Oral Biol. Med.* 4, 197-250.

Clark I M, Powell L K, Wright J K & Cawston T E (1991) Polyclonal and monoclonal antibodies against human tissue inhibitor of metalloproteinases (TIMP) and the design of an enzyme-linked immunosorbent assay to measure TIMP. *Matrix* 11, 76-85.

Cooksley S, Hipkiss J B, Tickle S P, Holmes I E, Docherty A J, Murphy G & Lawson A D (1990) lmmunoassays for the detection of human collagenase, stromelysin, tissue inhibitor of metalloproteinases (TIMP) and enzyme-inhibitor complexes. *Matrix* 10, 285-291.

Cooper T W, Eisen A Z, Stricklin G P & Welgus H G (1985) Platelet-derived collagenase inhibitor: characterization and subcellular localization. *Proc. Natl. Acad. Sci. U.S.A.* 82, 2779-2783.

DeClerck Y A, Perez N, Shimada H, Boone T C, Langley K E & Taylor S M (1992) Inhibition of invasion and metastasis in cells transfected with an inhibitor of metalloproteinases. *Cancer Res.* 52, 701-708.

Fujimoto N, Zhang J, Iwata K, Shinya T, Okada Y & Hayakawa T (1993) A one-step sandwich enzyme immunoassay for tissue inhibitor of metalloproteinases-2 using monoclonal antibodies. *Clin. Chim. Acta* 220, 31-45.

Goldberg G I, Strongin A,. Coltier I E, Genrich L T & Marmer B L (1992) Interaction of 92-kDa type IV collagenase with the tissue inhibitor of metalloproteinases prevents dimerization, complex formation with interstitial collagenase, and activation of the proenzyme with stromelysin. *J. Biol. Chem.* 267, 4583-4591.

Hembry R M, Murphy G & Reynolds J J (1985) Immunolocalization of tissue inhibitor of metalloproteinases (TIMP) in human cells. Characterization and use of a specific antiserum. *J. Cell Sci.* 73, 105-119.

Holten-Andersen M, Murphy G, Nielsen H J, Pedersen A N, Christensen I J, Høyer-Hansen G, Brünner N and Stephens R W (1999) Quantitation of TIMP-1 in plasma of healthy blood donors and patients with advanced cancer. *Br J Cancer* 80, 495-503.

Jung K, Nowak L, Lein M, Priem F, Schnorr D, Loening S A (1997) Matrix metalloproteinases 1 and 3, tissue inhibitor of metalloproteinase-1 and the complex of metalloproteinase-1/tissue inhibitor in plasma of patients with prostate cancer. *Int. J. Cancer* 74, 220-223.

Jung K, Nowak L, Lein M, Henke W, Schnorr D & Loening S A (1996) What kind of specimen should be selected for determining tissue inhibitor of metalloproteinase-1 (TIMP-1) in blood? [letter]. *Clin. Chim. Acta* 254, 97-100.

Jung K, Nowak L, Lein M, Henke W, Schnorr D & Loening S A (1996) Role of specimen collection in preanalytical variation of metalloproteinases and their inhibitors in blood. *Clin. Chem.* 42, 2043-2045.

Keyszer G, Lambiri I, Nagel R, Keysser C, Keysser M, Gromnica-Ihle E, Franz J, Burmester G R, Jung K (1999) Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers. *J. Rheum.* 26, 251-258.

Kjeldsen L, Bjerrum O W, Askaa J, Borregaard N (1992) Subcellular localization and release of human neutrophil gelatinase, confirming the existence of separate gelatinase-containing granules. *Biochem. J.* 287, 603-610.

Khokha R & Waterhouse P (1993) The role of tissue inhibitor of metalloproteinase-1 in specific aspects of cancer progression and reproduction. *J. Neurooncol.* 18, 123-127.

Khokha R, Zimmer M J, Graham C H, Lala P K & Waterhouse P (1992a) Suppression of invasion by inducible expression of tissue inhibitor of metalloproteinase-1 (TIMP-1) in B16-F10 melanoma cells. *J. Natl. Cancer Inst.* 84, 1017-1022.

Khokha R, Zimmer M J, Wilson S M & Chambers A F (1992b) Up-regulation of TIMP-1 expression in B16-F10 melanoma cells suppresses their metastatic ability in chick embryo. *Clin. Exp. Metastasis* 10, 365-370.

Kleiner Jr D E, Tuuttila A, Tryggvason K & Stetler-Stevenson W G (1993) Stability analysis of latent and active 72-kDa type IV collagenase: the role of tissue inhibitor of metalloproteinases-2 (TIMP-2). *Biochemistry* 32, 1583-1592.

Kodama S, Yamashita K, Kishi J, Iwata K & Hayakawa T (1989) A sandwich enzyme immunoassay for collagenase inhibitor using monoclonal antibodies. *Matrix* 9,1-6.

Liotta L A, Steeg P S & Stetler-Stevenson W G (1991) Cancer metastasis and angiogenesis: an imbalance of positive and negative regulation. *Cell* 64, 327-336.

MacDougall J R & Matrisian L M (1995) Contributions of tumor and stromal matrix metalloproteinases to tumor progression, invasion and metastasis. *Cancer Metastasis Rev.* 14, 351-362.

Matrisian L M (1992) The matrix-degrading metalloproteinases. *Bioessays* 14, 455-463.

Mimori K, Mori M, Shiraishi T, Fujie T, Baba K, Haraguchi M, Abe R, Ueo H & Akiyoshi T (1997) Clinical significance of tissue inhibitor of metalloproteinase expression in gastric carcinoma. *Br. J. Cancer* 76, 531-536.

Moll U M, Youngleib G L, Rosinski K B & Quigley J P (1990) Tumor promoter-stimulated Mr 92,000 gelatinase secreted by normal and malignant human cells: isolation and characterization of the enzyme from HT1080 tumor cells. *Cancer Res.* 50, 6162-6170.

Moutsiakis D, Mancuso P, Krutzsch H, Stetler-Stevenson W G & Zucker S (1992) Characterization of metalloproteinases and tissue inhibitors of metalloproteinases in human plasma. *Connect. Tissue Res.* 28, 213-230.

Murphy G, Houbrechts A, Cockett M I, Williamson R A, O'Shea M & Docherty A J (1991) The N-terminal domain of tissue inhibitor of metalloproteinases retains metalloproteinase inhibitory activity [published erratum appears in Biochemistry 1991 Oct. 22; 30(42):10362]. *Biochemistry* 30, 8097-8102.

Stetler-Stevenson W G, Hewitt R & Corcoran M (1996) Matrix metalloproteinases and tumor invasion: from correlation and causality to the clinic. *Semin. Cancer Biol.* 7, 147-154.

Stetler-Stevenson W G, Krutzsch H C & Liotta L A (1989) Tissue inhibitor of metalloproteinase (TIMP-2). A new member of the metalloproteinase inhibitor family. *J. Biol. Chem.* 264, 17374-17378.

Stetler-Stevenson W G, Liotta L A & Kleiner Jr D E (993), Extracellular matrix 6: role of matrix metalloproteinases in tumor invasion and metastasis. *FASEB J.* 7, 1434-1441.

Thorgeirsson U P, Lindsay C K, Cottam D W & Gomez D E (1993) Tumor invasion, proteolysis, and angiogenesis. *J. Neurooncol.* 18, 89-103.

Welgus H G, Jeffrey J J, Eisen A Z, Roswit W T & Stricklin G P (1985) Hurman, skin fibroblast collagenase: interaction with substrate and inhibitor. *Coll. Relat. Res.* 5, 167-179.

Wilhelm S M, Collier I E, Marmer B L, Eisen A Z, Grant G A & Goldberg G I (1989) SV40-transformed human lung fibroblasts secrete a 92-kDa type IV collagenase which is identical to that secreted by normal human macrophages [published erratum appears in J Biol Chem 1990 Dec. 25; 265(36):22570]. *J. Biol. Chem.* 264, 17213-17221.

Zucker S, Lysik R M, DiMassimo B I, Zarrabi H M, Moll U M, Grimson R, Tickle S P & Docherty A J (1995) Plasma assay of gelatinase B: tissue inhibitor of metalloproteinase complexes in cancer. *Cancer* 76, 700-708.

The invention claimed is:

1. A method for determining whether an individual is likely to have colorectal cancer, the method comprising:
   a. determining a total concentration of TIMP-1 in a plasma sample of said individual and determining a concentration of at least one additional marker different from any form of TIMP-1 in a body fluid sample of said individual,
   b. combining the total concentration of TIMP-1 in the plasma sample of said individual and the concentration of said at least one additional marker different from any form of TIMP-1 in the body fluid sample of said individual to result in a combined parameter of the individual,
   c. combining a total plasma concentration of TIMP-1 of a non-colorectal cancer population with a body fluid concentration of the at least one additional marker different from any form of TIMP-1 of a non-colorectal cancer population, the resulting combination being referred to herein as a non-colorectal cancer benchmark combined parameter,
   d. indicating the individual as likely to have colorectal cancer if the combined parameter of the individual is at or above said non-colorectal cancer benchmark combined parameter and indicating the individual as unlikely of having colorectal cancer if the combined parameter is below said non-colorectal cancer benchmark combined parameter and wherein the combining in the sub-sections b. and c. is performed by logistic regression analysis.

2. A method for determining whether an individual is likely to have colorectal cancer, the method comprising:
   a. determining a total concentration of TIMP-1 in a plasma sample of said individual and determining a concentration of at least one additional marker different from any form of TIMP-1 in a body fluid sample of said individual,
   b. combining the total concentration of TIMP-1 in the plasma sample of said individual and the concentration of said at least one additional marker different from any form of TIMP-1 in the body fluid sample of said individual to result in a combined parameter of the individual, c. combining a total plasma concentration of TIMP-1 of a non-colorectal cancer population with a body fluid concentration of at least one additional marker different from any form of TIMP-1 of a non-colorectal cancer population, the resulting combination being referred to herein as a non-colorectal cancer benchmark combined parameter, d. constructing a percentile plot of the non-colorectal cancer benchmark combined parameter, e. selecting a desired specificity, f. determining from the percentile plot the non-colorectal cancer benchmark combined parameter value corresponding to the desired specificity, and g. indicating the individual as likely to have colorectal cancer if the combined parameter of the individual is at or above said non-colorectal cancer benchmark combined parameter value corresponding to the desired specificity, and indicating the individual as unlikely of having colorectal cancer if the combined parameter of the individual is below said non-colorectal cancer benchmark combined parameter value corresponding to the desired specificity.

3. A method for determining whether an individual is likely to have colorectal cancer, the method comprising:

a. determining a total concentration of TIMP-1 in a plasma sample of said individual and determining a concentration of at least one additional marker different from any form of TIMP-1 in a body fluid sample of the individual, b. combining the total concentration of TIMP-1 in the plasma sample of said individual and the concentration of said least one additional marker different from any form of TIMP-1 in the body fluid sample of the individual to result in a combined parameter of the individual, c. combining a total plasma concentration of TIMP-1 in a plasma sample of a non-colorectal cancer population with a body fluid concentration of at least one additional marker different from any form of TIMP-1 of the non-colorectal cancer population, the resulting combination being referred to herein as a non-colorectal cancer benchmark combined parameter, d. combining a total concentration of TIMP-1 in a plasma sample in a population with known colorectal cancer with a body fluid concentration of at least one additional marker different from any form of TIMP-1 in a population with known colorectal cancer, the resulting combination being referred to herein as a colorectal cancer benchmark combined parameter, e. constructing a percentile plot of the non-colorectal cancer benchmark combined parameter, f. constructing a ROC (receiver operating characteristics) curve based on the non-colorectal cancer benchmark combined parameter and the colorectal cancer benchmark combined parameter, g. selecting a desired sensitivity, h. determining from the ROC curve the specificity corresponding to the desired sensitivity, i. determining from the percentile plot the non-colorectal cancer benchmark combined parameter value corresponding to the desired specificity, and j. indicating the individual as likely to have colorectal cancer if the combined parameter of the individual is at or above said non-colorectal cancer benchmark combined parameter value corresponding to the determined specificity and indicating the individual as unlikely to have colorectal cancer if the combined parameter of the individual is below the non-colorectal cancer benchmark parameter value corresponding to the determined specificity.

4. A method for determining whether an individual is likely to have colorectal cancer, the method comprising determining a total concentration of TIMP-1 in a plasma sample of said individual and determining a concentration of at least one additional marker different from any form of TIMP-1 in a body fluid sample of said individual, and indicating the individual as likely to have colorectal cancer if the combination of the total concentration of TIMP-1 in the plasma sample of the individual and the concentration of the at least one additional marker different from any form of TIMP-1 in the body fluid sample of the individual is at or above a combination of a total plasma concentration of TIMP-1 in a non-colorectal cancer population and a body fluid concentration of at least one additional marker different from any form of TIMP-1 measured in the non-colorectal cancer population, and indicating the individual as unlikely to have colorectal cancer if the combination of the total concentration of TIMP-1 in the plasma sample of the individual and the concentration of the at least one additional marker different from any form of TIMP-1 in the body fluid sample of the individual is lower than the combination of the total plasma concentration of TIMP-1 and the body fluid concentration of at least one additional marker different from any form of TIMP-1 measured in the non-colorectal cancer population and wherein the combination is performed by logistic regression analysis.

5. A method according to claim 1, 2, 3 or 4, wherein the body fluid is selected from the group consisting of blood, serum, plasma, faeces, urine and cerebrospinal fluid.

6. A method according to claim 5, wherein the body fluid is blood.

7. A method according to claim 5, wherein the body fluid is urine.

8. A method according to claim 5, wherein the concentration determination of the total TIMP-1 and of the at least one additional marker different from any form of TIMP-1 of said individual is performed by means of an immuno assay or an activity assay.

9. A method according to claim 8, wherein the activity assay is zymography.

10. A method according to claim 1, 2 or 3, wherein the total concentration of TIMP-1 in the plasma of the non-colorectal cancer population and the concentration of the at least one additional marker different from any form of TIMP-1 in the body fluid sample of the non-colorectal cancer population are determined prior to the sub-section c).

11. A method according to any one of claims 1-4 wherein the total plasma concentration of TIMP-1 in the plasma sample of the individual comprises the sum of TIMP-1 in free form and TIMP-1 in complex forms and the total plasma concentration of TIMP-1 of the non-colorectal cancer population comprises the sum of TIMP-1 in free form and TIMP-1 in complex forms.

12. A method according to claim 1, 2 or 3, wherein the non-colorectal cancer benchmark combined parameter is further combined with a concentration of free TIMP-1 in a plasma sample of the non-colorectal cancer population, and the combined parameter of the individual is further combined with a concentration of free TIMP-1 in a plasma sample of the individual.

13. A method according to claim 12, wherein the total plasma concentration of TIMP-1 of the non-colorectal cancer population and the concentration of the free TIMP-1 in the plasma sample of the non-colorectal cancer population are determined prior to the sub-section c).

14. A method according to claim 2, or 3, wherein the combining in the sub-sections b. and c. of claim 2 and in the subsections b., c., and d. of claim 3 is performed by logistic regression analysis.

15. A method according to claim 1, 2, 3 or 4 wherein the at least one additional marker is a tumour marker.

16. A method according to claim 15 wherein the tumour marker is selected from the group consisting of CEA, soluble u-PAR, cathepsin B, HER2-neu, CA15-3 and YKL-40.

17. A method according to claim 16, wherein the tumour marker is the concentration of CEA.

18. A method according to claim 1, 2, 3 or 4, wherein the individual is a member of an unselected population.

19. A method according to claim 1, 2, 3 or 4, wherein the individual is a member of a population already identified as having an increased risk of developing cancer.

20. A method according to claim 1, 2, 3 or 4 wherein the colorectal cancer is early stage colorectal cancer.

21. A method according to claim 20, wherein the early stage colorectal cancer is selected from the group consisting of colon cancer Dukes' stage A, colon cancer Dukes' stage B, colon cancer Dukes' stage C, rectal cancer Dukes' stage A, rectal cancer Dukes' stage B and rectal cancer Dukes' stage C.

22. A method according to claim 1, 2, 3 or 4, wherein the determination of the total concentration of TIMP-1 in the plasma sample of the individual and the determination of the concentration of the least one additional marker different from any form of TIMP-1 in the body fluid sample of the individual is performed by means of an immuno assay.

23. A method according to claim 22, wherein said immuno assay is ELISA.

24. A method of claim 1, 2, 3 or 4, wherein the total plasma concentration of TIMP-1 of the non-colorectal cancer population is obtained from individuals of the non-colorectal cancer population and the body fluid concentration of the at least one additional marker different from any form of TIMP-1 of the non-colorectal cancer population is obtained from individuals of the non-colorectal cancer population.

25. A method of claim 12, wherein the concentration of free TIMP-1 in the plasma sample of the non-colorectal cancer population is obtained from individuals of the non-colorectal cancer population.

26. A method according to claim 19, wherein the individual has a genetic disposition for colorectal cancer, has been exposed to carcinogenic substances or has a colorectal cancer-predisposing non-malignant disease.

27. A method according to claim 19, wherein the individual is selected from the group consisting of: an individual who had a polyp, an individual with Crohn's disease, an individual with an ulcerative colitis, and an individual with one or more family members with colorectal cancer.

28. A method according to claim 17, wherein the sensitivity of the combination of the total concentration of TIMP-1 in the plasma sample of said individual and the concentration of said CEA determined by logistic regression analysis is 52%, at 98% specificity, compared to sensitivity of 35% at 98% specificity for CEA only.

29. A method according to claim 1, 2, 3 or 4, wherein, if the individual is indicated to be likely to have colorectal cancer, the individual is referred for further examination.

* * * * *